(12) United States Patent
Beazley et al.

(10) Patent No.: US 8,686,230 B2
(45) Date of Patent: *Apr. 1, 2014

(54) CORN PLANT MON88017 AND COMPOSITIONS AND METHODS FOR DETECTION THEREOF

(75) Inventors: Kim A. Beazley, Kirkwood, MO (US); Timothy R. Coombe, Ellisville, MO (US); Mark E. Groth, St. Louis, MO (US); Terri B. Hinchey, Mystic, CT (US); Jay C. Pershing, Webster Groves, MO (US); Ty T. Vaughn, Imperial, MO (US); Bei Zhang, Ballwin, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/529,933

(22) Filed: Jun. 21, 2012

(65) Prior Publication Data

US 2013/0031679 A1     Jan. 31, 2013

Related U.S. Application Data

(62) Division of application No. 10/582,007, filed as application No. PCT/US2004/041723 on Dec. 14, 2004, now Pat. No. 8,212,113.

(60) Provisional application No. 60/529,477, filed on Dec. 15, 2003.

(51) Int. Cl.
    *C12N 15/82*      (2006.01)
    *C12N 15/52*      (2006.01)
    *C07H 21/04*      (2006.01)

(52) U.S. Cl.
    USPC ....... 800/300.1; 536/23.2; 536/24.3; 800/298

(58) Field of Classification Search
    None
    See application file for complete search history.

(56) References Cited

U.S. PATENT DOCUMENTS

| 4,808,426 | A  |   | 2/1989  | Strop et al. |
| 5,428,147 | A  |   | 6/1995  | Barker et al. |
| 5,633,435 | A  | * | 5/1997  | Barry et al. ................ 800/288 |
| 6,063,597 | A  |   | 5/2000  | English et al. |
| 6,501,009 | B1 |   | 12/2002 | Romano |
| 6,551,962 | B1 |   | 4/2003  | Pershing et al. |
| 7,705,216 | B2 |   | 4/2010  | Cavato |

(Continued)

FOREIGN PATENT DOCUMENTS

| EP | 1167531     | 1/2002 |
| WO | WO 92/04449 | 3/1992 |

(Continued)

OTHER PUBLICATIONS

Chevallier, Andrew; "Maize", The Encyclopedia of Medicinal Plants; 125, 2000.

(Continued)

*Primary Examiner* — David H Kruse
(74) *Attorney, Agent, or Firm* — Dentons US LLP; Pamela Sisson

(57) ABSTRACT

The present invention provides a corn plant designated MON88017 and DNA compositions contained therein. Also provided are assays for detecting the presence of the corn plant MON88017 based on a DNA sequence and the use of this DNA sequence as a molecular marker in a DNA detection method.

11 Claims, 10 Drawing Sheets

(56) References Cited

U.S. PATENT DOCUMENTS

| | | |
|---|---|---|
| 8,212,113 B2 * | 7/2012 | Beazley et al. ............ 800/300.1 |
| 2002/0013960 A1 | 1/2002 | Behr et al. |
| 2002/0102582 A1 | 8/2002 | Levine |

FOREIGN PATENT DOCUMENTS

| | | |
|---|---|---|
| WO | WO 98/31838 | 7/1998 |
| WO | WO 99/31248 | 6/1999 |
| WO | WO 00/11185 | 3/2000 |
| WO | WO 2005/059103 A2 | 6/2005 |

OTHER PUBLICATIONS

Chevallier, Andrew; "Maize", English translation of Line 6, The Encyclopedia of Medicinal Plants; 125, 2000.

Database Geneseq (online); "Human Skin EST 6332"; XP002469826 retrieved from EBI accession No. GSN:ABV68546 Database accession No. ABV68546, Oct. 21, 2002.

Database EMBL (online); "Method for Analyzing Quantitative Expression of Genes"; XP002469827 retrieved from EBI accession No. EMBL:BD071106 Database accession No. EMBL:BD071106, Sep. 4, 2002.

Database Geneseq (online); "Oligonucleotide SEQ ID No. 9593 for Detecting SNP TSC0002512"; XP002469952 retrieved from EBI accession No. GSN:ABC09602 Database accession No. ABC09602, Feb. 20, 2002.

Database Geneseq (online); "Oligonucleotide SEQ ID No. 9594 for Detecting SNP TSC0002512"; XP002469951 retrieved from EBI accession No. GSN:ABC09603 Database accession No. ABC09603, Feb. 20, 2002.

Ditto, M.D.; Biotechnology Consultation Note to the File BNF No. 000075 (online), XP002469825; retrieved from the Internet at URL:www.cfsan.fda.gov/{rdb.bnfm075.html, Dec. 31, 2001.

Francois, et al.; "Different 1-4, 6, Approaches for Multi-Transgene Stacking in 15, 16 Plants", *Plant Science*, 163:281-295, 2002.

GenBank Accession No. BZ546419;Whitelaw et al., Dec. 16, 2002.

McElroy, "Moving agbiotech downstream", *Nature Biotechnology*, 17(11):1071-1074, 1999.

Mumm et al., "Quality control in the development of transgenic crop seed products", *Crop Science*, 41(5):1381-1389, 2001.

New England BioLabs Inc. 1998/99 Catalog, (NEB Catalog), pp. 121 and 284, 1999.

Paul et al., "Transgenic maize", *Starch*, 57(5):187-195, 2005.

Sidhu, R.S.; "Petition for the Determination of Nonregulated Status for MON88017 Corn", #04-CR-108U 1-277, 2004.

USPTO; Final Office Action regarding U.S. Appl. No. 11/801,114, Aug. 26, 2009.

Windels et al.; Eur. Food. Res. Technol. 213: 107-112, 2001.

* cited by examiner

```
GACCAGCGTCTCCCGCCGCACCCGCAGTCTGCACCGTAGAGATCGGATGTACAGGCA
TGTAGCATTAGGCTATTCAGCGGCTCTCGTATCTTATTCCCTACCATCTATTTTATC
TACACTGTATAATACTCCCTCCGTTTATTGTTTATTTGTCGTTGAATAGTTCAATAT
TTGCACTGTCCAGCGACAACTAAAATGAAACGGAGTGAGGTAGTGTTTTGTACAACC
ATATATAGAGGTGCCCAAACGGGCGGCCCGGCCCGGGCCCGTCAGGCCCGACGGTTA
ATCGGGCCGTGCCCGGCCGGCCCCGTGCCGTAGCCGTGGCCCAGGCACGGCGTGCCG
GGCCAGCCGTTTAACTGGTCACGTTCTCCCGCCTAACTGAAGGACACTAACCAATAT
AACTCGTGAGCATTTGTTGTAAATAGCTAATATAAAATGTAAATATATATACTATGT
TTTATAAAATAAAAAATATATAATCGTGCCGGCCAGGCCGGCACTGCGGGCCAAGAC
AGCGGCCCAAGCACGTCACGGTTCTCGTGCCGGGCCGGCCCCGGCATCGTGTTTCAG
GCCGGTCCGTTAGGCACGGCTCATTTGGCCCTCTATAACCATATATCATATTCATCG
ACGACCTTGGGCTAAGGCAGACCGACGGCCGCCCTAGGCCCCAGATCTATAGAGGCT
TAATGCTAAATATAAATTCAGTAGTTAGACTATCAATGTATGATATAATAGTTTAGC
AACAAAATACTAAAGAATTTATGGCTACGATGTTTTCATAATCCGATCTTATCTAAA
CATGTTAGAAGGAAATTTTAAAGTAATATTATAATATGTATCTTTTTATTTACTTAT
TGCTTGATATAGATATTTTTGATCTATCTTAAGTGTTTTATATTGATAATATTTATG
TATATAAAGAATTAGAATAGTCCTATTTTAAATTTTGTC**CTGAACCCCTAAAATCCC
AGG**ACCGCCACCTATCATATACATACATGATCTTCTAAATACCCGATCAGAGCGCTA
AGCAGCAGAATCGTGTGACAACGCTAGCAGCTCTCCTCCAACACATCATCGACAAGC
ACCTTTTTTGCCGGAGTATGACGGTGACGATATATTCAATTGTAAATGGCTTCATGT
CCGGGAAATCTACATGGATCAGCAATGAGTATGATGGTCAATATGGAGAAAAAGAAA
GAGTAATTACCAATTTTTTTTCAATTCAAAAATGTAGATGTCCGCAGCGTTATTATA
AAATGAAAGTACATTTTGATAAAACGACAAATTACGATCCGTCGTATTTATAGGCGA
AAGCAATAAACAAATTATTCTAATTCGGAAATCTTTATTTCGACGTGTCTACATTCA
CGTCCAAATGGGGCTTAGATGAGAAACTTCACGATTTGGCGCGCCAAAGCTTACTC
GAGGTCATTCATATGCTTGAGAAGAGAGTCGGGATA
```

Figure 3

```
CAAACTCCACATGGGCTTCTCGGGCGACAAGAATGAACTGATCATTGGTGCTGAGTC
CTTCGTCTCCAACGAGAAGATCTACATCGACAAGATCGAGTTCATCCCCGTCCAGCT
GTGATAGGAACTCTGATTGAATTCTGCATGCGTTTGGACGTATGCTCATTCAGGTTG
GAGCCAATTTGGTTGATGTGTGTGCGAGTTCTTGCGAGTCTGATGAGACATCTCTGT
ATTGTGTTTCTTTCCCCAGTGTTTTCTGTACTTGTGTAATCGGCTAATCGCCAACAG
ATTCGGCGATGAATAAATGAGAAATAAATTGTTCTGATTTTGAGTGCAAAAAAAAAG
GAATTAGATCTGTGTGTGTTTTTTGGATCCCCGGGGCGGCCGCTCGAGCAGGACCTG
CAGAAGCTAGCTTGATGGGGATCAGATTGTCGTTTCCCGCCTTCAGTTTAAACAGAG
TCGGGTTTGGATGGTCAACTCCGGCATACTGCCGAAAACAAACCAATCCGTCACCGT
CAAGGCCCCGCACCGCTGGCCGCACGCAGGAAAAATAAGTTGCGACCGCGAGCGGGC
GAATCAGAAAGGGCGTCCGGCCTTGGTCAGACACGACAGCGACGCGGAAAGGCTGCG
CCCGCGGTGCCATCTACAAGGGTCCACGTCCATCCAAAAGAGCGGTGCCCTGGACT
TCTCCCTCGTGTTCCTACTTCCTACGCGAAGGAAGCCAGGCAGGTGCGCAGCTTTTC
CAACCTTCCACCCCCCCGTGCGGCGCTCCACGCTGAGTCGCTGACCGCTCGCGCC
TCTCTTCGCCTCCTCCTCACTCGCCGCGTCCTCCGCAGCACAGCCCACTCGCATCGG
ATCGCGCGCGGGGAGCGGCATGGCCGGCGACGACGGCAGCGGCGGGAGCGGAGGCGG
CAACAGGGAGGACGAGGTCCACGTGCAGATCGCAGGTCAGTGTCAGTCCTCCGCTCG
TTCTCTCTCTCTCCGACGGACAGTGTGAACTATGTCGGGTCGTCGTTGAGGATGCGA
TGAGAGGAGCGCGGGAAGGACTGTCGTAGATTGGATTTGCTCTGCAGTGCGTGGGTA
GCCCCGAGTCCCCGACACATGTTCTTTTTTCTCGGGTTATGTCAGCGGCGGTACGTC
GTTGGAACGCTCAAGCGCGAGAGGTGTTCGATGAATTACCTTCTGGTGTGTGGCGTA
CCGGTGGGTCAGTGGGGTTTTTGGTTCGTGTACGGGATTTGGGGTTGGGGGTCATCT
CCCTTCTTCAGTGCGCGCGCTCACGAGTCACGGCTGTCTTGTGATTGCTGCATCTGT
GCCATGTGCTCGTGCGTGCGTTTTCAGTTACTGGCCATTGACACTGAGTGAATGTTC
GGTTGGTCGTCCGATAGGGTTGGTTCAGCTGTTAATTACGACTCCAAGTATCTGAAA
CATTTCATGAGGATGTGTAGGGAACCTTACTTTATGCACTTCAATGGCCAGGCCAGG
CCTGTATTATCTTTTTCTTGTTTGGGAATAATGATGTGAGCTTTAGGGGAGCAGCGC
TGCTTCTTCTTTTTTTTTCTCCAGAAAAAGTCATAGATATACCGTGGACAATTTCT
TTGTGTGCGGTAATTTTAGAGCACTGTGGGTTTGTGCCCTGTTCGTCAGGAAAAGTA
CCCAAGCTGGGATTTCACTTGGGTCTAAGAAACCAGCGTTTCAGTTTGGGGGGTCTC
CTGGTACCCTGAAGTGCTTACCATTTATAGTTCCCGGATGACCTGTTCATAATGCCT
TCTGTATGTTGTTTGCAGGATCATCCAAACCTGAAACCTCATCTACCAACGAAACAG
CTCCTCAAAACTCTCATACCAAGCATTGGCATTGGTGGCTGATGGTAACTCTGAACA
TTTTCTTCCTCGTTGCTGGTCAGACAGCATCGACACTCCTTGGCAGGTTCTACTACA
ACCAAGGTGGAAATAGCAAGTGGATGTCCACATTTGTCCAAACCGCTGGCTTTCCAG
TGCTGTTCGTCGCCCTATATCTGTTCCGTTCAAAATCGCCTTCTACACAAACAACCA
CCAGTAACCCTGAGACTTCTGTCACCAAAATTACTCTTATATATGTTGTCTTGGGCC
TCATCATTGCTGCCGATGACTTGATGTATTCCTATGGCCTGTTGTACCTTCCTGTAT
CAACATATTCGCTCATTTGCGCTAGTCAGCTGGCCTTCAATGCTGTCTTCTCATATG
TCCTAAATGCTCAAAAGTTCACCCCATTCATTTTCAACTCAGTAATTCTCCTTACTT
TTCCCGCTGCGCTTCTTGGAGTTGACGAAGATTCTCAGGGTACCAATGGTTTATCGC
GTGGGAAGTACATATTGGGTTTCGCATTGACCCTAGGAGCCTCGGCCACATACTCAC
TAATTCTCTCTCTAATGCAAGTCGCATTCGAGAAGGTTATTAAGAAGGAAACTTTCT
CAGTCGTGTTGAATATGCAGATATATACAGCACTAGTGGCAACAGTAGCTTCTCTTA
TCGGTTTATTTGCAAGCGGCGAGTGGAAG
```

Figure 4A

ACTTTAGAGGGAGAGATGCATGCCTTCAGCTCAGGGAGGGTGTCCTATGTGATGACA
CTTCTATGGACTGCTGTATCTTGGCAGATAGCTTCCGTAGGAGTGGTGGGTTTGATC
TTTG
TTGTGTCATCACTCTTTTCAAATGTGATAAGCACACTGGCTCTACCCATCATTCCGA
TTTTTGCTGTGATTTTCTTCCACGACAAGATGGATGGAGTGAAGATTATTGCTATGT
TGATGGCCATCTGGGGATTCGTTTCATATGGATATCAATTATATGTCAGTGACAAGA
AGGCTAGGAAGACTTCAGTCAGTGTGGAGGAGAATTCCTAAGCGCTTGTTGGCCTGT
TACATTGGTCTTTGTGGCTCCTATACCACTTTAAGTTGCTGGTATTGAGGAGGTACT
AGTTATTGACTTATTGTATCCAAAAGGAGCTCAGTTGAGAATCTCAGGTTTACACAA
TTCATAGGTATATACTTCTGTTAGTATTGTCATATCATCATATGTACCGATGTACGG
TTGTGTTGTCCTTTAAAATAAAAAGATTAGCATTTCCAGAGGCATGCTCTCTAGATT
TCTAATTGCCTTAAATATTTTCTTGCCTTTGTTTTGTTTTTTTTTTTTGCTATTAA
CTGTGATTTGTGATTCTATGGTTTGACATATAGTATTTCTAGGTGGTGTGCATGCTG
ATCCTGCTTATTCTACTATGAATTAAATGCAGTATAGGTCCATTAACTTTTGCATGC
GAGCTTCTTGGTGAAAGCCCTGCGTGGTTTGGTTTTGATAACTGAGTGACAGTTAGT
AAAGGTTTTTTGTGTACCACATTTTCTTAGTGTTCTTCACTCCAAATTTGATAGGCG
AGGCTCGATCTTATTCAGTTGCTTGGCTTTCCTTGTTATAACGCCTCAGCTAATCTG
GCTTTGTTTCCTTATGCATACCTTCTGTAATCTAACACCAAACCACAGATGTTGCAT
GTCCATTCTCCATGG

Figure 4B

```
   1 TACCCGATCA GAGCGCTAAG CAGCAGAATC GTGTGACAAC GCTAGCAGCT
  51 CTCCTCCAAC ACATCATCGA CAAGCACCTT TTTTGCCGGA GTATGACGGT
 101 GACGATATAT TCAATTGTAA ATGGCTTCAT GTCCGGGAAA TCTACATGGA
 151 TCAGCAATGA GTATGATGGT CAATATGGAG AAAAAGAAAG AGTAATTACC
 201 AATTTTTTTT CAATTCAAAA ATGTAGATGT CCGCAGCGTT ATTATAAAAT
 251 GAAAGTACAT TTTGATAAAA CGACAAATTA CGATCCGTCG TATTTATAGG
 301 CGAAAGCAAT AAACAAATTA TTCTAATTCG GAAATCTTTA TTTCGACGTG
 351 TCTACATTCA CGTCCAAATG GGGGCTTAGA TGAGAAACTT CACGATTTGG
 401 CGCGCCAAAG CTTACTCGAG GTCATTCATA TGCTTGAGAA GAGAGTCGGG
 451 ATAGTCCAAA ATAAAACAAA GGTAAGATTA CCTGGTCAAA AGTGAAAACA
 501 TCAGTTAAAA GGTGGTATAA AGTAAAATAT CGGTAATAAA AGGTGGCCCA
 551 AAGTGAAATT TACTCTTTTC TACTATTATA AAAATTGAGG ATGTTTTTGT
 601 CGGTACTTTG ATACGTCATT TTTGTATGAA TTGGTTTTTA AGTTTATTCG
 651 CTTTTGGAAA TGCATATCTG TATTTGAGTC GGGTTTTAAG TTCGTTTGCT
 701 TTTGTAAATA CAGAGGGATT TGTATAAGAA ATATCTTTAG AAAAACCCAT
 751 ATGCTAATTT GACATAATTT TTGAGAAAAA TATATATTCA GGCGAATTCT
 801 CACAATGAAC AATAATAAGA TTAAAATAGC TTTCCCCCGT TGCAGCGCAT
 851 GGGTATTTTT TCTAGTAAAA ATAAAGATA  AACTTAGACT CAAAACATTT
 901 ACAAAAACAA CCCCTAAAGT TCCTAAAGCC CAAAGTGCTA TCCACGATCC
 951 ATAGCAAGCC CAGCCCAACC CAACCCAACC CAACCCACCC CAGTCCAGCC
1001 AACTGGACAA TAGTCTCCAC ACCCCCCCAC TATCACCGTG AGTTGTCCGC
1051 ACGCACCGCA CGTCTCGCAG CCAAAAAAAA AAAGAAAGAA AAAAAGAAA
1101 AAGAAAAAAC AGCAGGTGGG TCCGGGTCGT GGGGGCCGGA AACGCGAGGA
1151 GGATCGCGAG CCAGCGACGA GGCCGGCCCT CCCTCCGCTT CCAAAGAAAC
1201 GCCCCCCATC GCCACTATAT ACATACCCCC CCCTCTCCTC CCATCCCCCC
1251 AACCCTACCA CCACCACCAC CACCACCTCC ACCTCCTCCC CCCTCGCTGC
1301 CGGACGACGA GCTCCTCCCC CCTCCCCCTC CGCCGCCGCC GCGCCGGTAA
1351 CCACCCCGCC CCTCTCCTCT TTCTTTCTCC GTTTTTTTTT CCGTCTCGGT
1401 CTCGATCTTT GGCCTTGGTA GTTTGGGTGG GCGAGAGGCG GCTTCGTGCG
1451 CGCCCAGATC GGTGCGCGGG AGGGGCGGGA TCTCGCGGCT GGGGCTCTCG
```

Figure 5A

```
1501  CCGGCGTGGA TCCGGCCCGG ATCTCGCGGG GAATGGGGCT CTCGGATGTA
1551  GATCTGCGAT CCGCCGTTGT TGGGGGAGAT GATGGGGGGT TTAAAATTTC
1601  CGCCGTGCTA AACAAGATCA GGAAGAGGGG AAAAGGGCAC TATGGTTTAT
1651  ATTTTTATAT ATTTCTGCTG CTTCGTCAGG CTTAGATGTG CTAGATCTTT
1701  CTTTCTTCTT TTTGTGGGTA GAATTTGAAT CCCTCAGCAT TGTTCATCGG
1751  TAGTTTTTCT TTTCATGATT TGTGACAAAT GCAGCCTCGT GCGGAGCTTT
1801  TTTGTAGGTA GAAGTGATCA ACCATGGCGC AAGTTAGCAG AATCTGCAAT
1851  GGTGTGCAGA ACCCATCTCT TATCTCCAAT CTCTCGAAAT CCAGTCAACG
1901  CAAATCTCCC TTATCGGTTT CTCTGAAGAC GCAGCAGCAT CCACGAGCTT
1951  ATCCGATTTC GTCGTCGTGG GGATTGAAGA AGAGTGGGAT GACGTTAATT
2001  GGCTCTGAGC TTCGTCCTCT TAAGGTCATG TCTTCTGTTT CCACGGCGTG
2051  CATGCTTCAC GGTGCAAGCA GCCGGCCCGC AACCGCCCGC AAATCCTCTG
2101  GCCTTTCCGG AACCGTCCGC ATTCCCGGCG ACAAGTCGAT CTCCCACCGG
2151  TCCTTCATGT TCGGCGGTCT CGCGAGCGGT GAAACGCGCA TCACCGGCCT
2201  TCTGGAAGGC GAGGACGTCA TCAATACGGG CAAGGCCATG CAGGCGATGG
2251  GCGCCCGCAT CCGTAAGGAA GGCGACACCT GGATCATCGA TGGCGTCGGC
2301  AATGGCGGCC TCCTGGCGCC TGAGGCGCCG CTCGATTTCG GCAATGCCGC
2351  CACGGGCTGC CGCCTGACGA TGGGCCTCGT CGGGGTCTAC GATTTCGACA
2401  GCACCTTCAT CGGCGACGCC TCGCTCACAA AGCGCCCGAT GGGCCGCGTG
2451  TTGAACCCGC TGCGCGAAAT GGGCGTGCAG GTGAAATCGG AAGACGGTGA
2501  CCGTCTTCCC GTTACCTTGC GCGGGCCGAA GACGCCGACG CCGATCACCT
2551  ACCGCGTGCC GATGGCCTCC GCACAGGTGA AGTCCGCCGT GCTGCTCGCC
2601  GGCCTCAACA CGCCCGGCAT CACGACGGTC ATCGAGCCGA TCATGACGCG
2651  CGATCATACG GAAAAGATGC TGCAGGGCTT TGGCGCCAAC CTTACCGTCG
2701  AGACGGATGC GGACGGCGTG CGCACCATCC GCCTGGAAGG CCGCGGCAAG
2751  CTCACCGGCC AAGTCATCGA CGTGCCGGGC GACCCGTCCT CGACGGCCTT
2801  CCCGCTGGTT GCGGCCCTGC TTGTTCCGGG CTCCGACGTC ACCATCCTCA
2851  ACGTGCTGAT GAACCCCACC CGCACCGGCC TCATCCTGAC GCTGCAGGAA
2901  ATGGGCGCCG ACATCGAAGT CATCAACCCG CGCCTTGCCG GCGGCGAAGA
2951  CGTGGCGGAC CTGCGCGTTC GCTCCTCCAC GCTGAAGGGC GTCACGGTGC
```

Figure 5B

```
3001  CGGAAGACCG CGCGCCTTCG ATGATCGACG AATATCCGAT TCTCGCTGTC
3051  GCCGCCGCCT TCGCGGAAGG GGCGACCGTG ATGAACGGTC TGGAAGAACT
3101  CCGCGTCAAG GAAAGCGACC GCCTCTCGGC CGTCGCCAAT GGCCTCAAGC
3151  TCAATGGCGT GGATTGCGAT GAGGGCGAGA CGTCGCTCGT CGTGCGTGGC
3201  CGCCCTGACG GCAAGGGGCT CGGCAACGCC TCGGGCGCCG CCGTCGCCAC
3251  CCATCTCGAT CACCGCATCG CCATGAGCTT CCTCGTCATG GGCCTCGTGT
3301  CGGAAAACCC TGTCACGGTG GACGATGCCA CGATGATCGC CACGAGCTTC
3351  CCGGAGTTCA TGGACCTGAT GGCCGGGCTG GGCGCGAAGA TCGAACTCTC
3401  CGATACGAAG GCTGCCTGAT GAGCTCGAAT TCCCGATCGT TCAAACATTT
3451  GGCAATAAAG TTTCTTAAGA TTGAATCCTG TTGCCGGTCT TGCGATGATT
3501  ATCATATAAT TTCTGTTGAA TTACGTTAAG CATGTAATAA TTAACATGTA
3551  ATGCATGACG TTATTTATGA GATGGGTTTT TATGATTAGA GTCCCGCAAT
3601  TATACATTTA ATACGCGATA GAAAACAAAA TATAGCGCGC AAACTAGGAT
3651  AAATTATCGC GCGCGGTGTC ATCTATGTTA CTAGATCGGG GATTTGCGGC
3701  CGCGTTAACA AGCTTCTGCA GGTCCGATTG AGACTTTTCA ACAAAGGGTA
3751  ATATCCGGAA ACCTCCTCGG ATTCCATTGC CCAGCTATCT GTCACTTTAT
3801  TGTGAAGATA GTGGAAAAGG AAGGTGGCTC CTACAAATGC CATCATTGCG
3851  ATAAAGGAAA GGCCATCGTT GAAGATGCCT CTGCCGACAG TGGTCCCAAA
3901  GATGGACCCC CACCCACGAG GAGCATCGTG GAAAAGAAG ACGTTCCAAC
3951  CACGTCTTCA AAGCAAGTGG ATTGATGTGA TGGTCCGATT GAGACTTTTC
4001  AACAAAGGGT AATATCCGGA AACCTCCTCG GATTCCATTG CCCAGCTATC
4051  TGTCACTTTA TTGTGAAGAT AGTGGAAAAG GAAGGTGGCT CCTACAAATG
4101  CCATCATTGC GATAAAGGAA AGGCCATCGT TGAAGATGCC TCTGCCGACA
4151  GTGGTCCCAA AGATGGACCC CCACCCACGA GGAGCATCGT GGAAAAAGAA
4201  GACGTTCCAA CCACGTCTTC AAAGCAAGTG GATTGATGTG ATATCTCCAC
4251  TGACGTAAGG GATGACGCAC AATCCCACTA TCCTTCGCAA GACCCTTCCT
4301  CTATATAAGG AAGTTCATTT CATTTGGAGA GGACACGCTG ACAAGCTGAC
4351  TCTAGCAGAT CCTCTAGAAC CATCTTCCAC ACACTCAAGC CACACTATTG
4401  GAGAACACAC AGGGACAACA CACCATAAGA TCCAAGGGAG GCCTCCGCCG
4451  CCGCCGGTAA CCACCCCGCC CCTCTCCTCT TTCTTTCTCC GTTTTTTTTT
```

Figure 5C

```
4501  CCGTCTCGGT CTCGATCTTT GGCCTTGGTA GTTTGGGTGG GCGAGAGGCG
4551  GCTTCGTGCG CGCCCAGATC GGTGCGCGGG AGGGGCGGGA TCTCGCGGCT
4601  GGGGCTCTCG CCGGCGTGGA TCCGGCCCGG ATCTCGCGGG GAATGGGGCT
4651  CTCGGATGTA GATCTGCGAT CCGCCGTTGT TGGGGAGAT GATGGGGGGT
4701  TTAAAATTTC CGCCGTGCTA AACAAGATCA GGAAGAGGGG AAAAGGGCAC
4751  TATGGTTTAT ATTTTTATAT ATTTCTGCTG CTTCGTCAGG CTTAGATGTG
4801  CTAGATCTTT CTTTCTTCTT TTTGTGGGTA GAATTTGAAT CCCTCAGCAT
4851  TGTTCATCGG TAGTTTTTCT TTTCATGATT TGTGACAAAT GCAGCCTCGT
4901  GCGGAGCTTT TTTGTAGGTA GAAGTGATCA ACCATGGCCA ACCCCAACAA
4951  TCGCTCCGAG CACGACACGA TCAAGGTCAC CCCCAACTCC GAGCTCCAGA
5001  CCAACCACAA CCAGTACCCG CTGGCCGACA ACCCCAACTC CACCCTGGAA
5051  GAGCTGAACT ACAAGGAGTT CCTGCGCATG ACCGAGGACT CCTCCACGGA
5101  GGTCCTGGAC AACTCCACCG TCAAGGACGC CGTCGGGACC GGCATCTCCG
5151  TCGTTGGGCA GATCCTGGGC GTCGTTGGCG TCCCCTTCGC AGGTGCTCTC
5201  ACCTCCTTCT ACCAGTCCTT CCTGAACACC ATCTGGCCCT CCGACGCCGA
5251  CCCCTGGAAG GCCTTCATGG CCCAAGTCGA AGTCCTGATC GACAAGAAGA
5301  TCGAGGAGTA CGCCAAGTCC AAGGCCCTGG CCGAGCTGCA AGGCCTGCAA
5351  AACAACTTCG AGGACTACGT CAACGCGCTG AACTCCTGGA AGAAGACGCC
5401  TCTGTCCCTG CGCTCCAAGC GCTCCCAGGA CCGCATCCGC GAGCTGTTCT
5451  CCCAGGCCGA GTCCCACTTC CGCAACTCCA TGCCGTCCTT CGCCGTCTCC
5501  AAGTTCGAGG TCCTGTTCCT GCCCACCTAC GCCCAGGCTG CCAACACCCA
5551  CCTCCTGTTG CTGAAGGACG CCCAGGTCTT CGGCGAGGAA TGGGGCTACT
5601  CCTCGGAGGA CGTCGCCGAG TTCTACCGTC GCCAGCTGAA GCTGACCCAA
5651  CAGTACACCG ACCACTGCGT CAACTGGTAC AACGTCGGCC TGAACGGCCT
5701  GAGGGGCTCC ACCTACGACG CATGGGTCAA GTTCAACCGC TTCCGCAGGG
5751  AGATGACCCT GACCGTCCTG GACCTGATCG TCCTGTTCCC CTTCTACGAC
5801  ATCCGCCTGT ACTCCAAGGG CGTCAAGACC GAGCTGACCC GCGACATCTT
5851  CACGGACCCC ATCTTCCTGC TCACGACCCT CCAGAAGTAC GGTCCCACCT
5901  TCCTGTCCAT CGAGAACTCC ATCCGCAAGC CCACCTGTT CGACTACCTC
5951  CAGGGCATCG AGTTCCACAC GCGCCTGAGG CCAGGCTACT TCGGCAAGGA
```

Figure 5D

```
6001  CTCCTTCAAC TACTGGTCCG GCAACTACGT CGAGACCAGG CCCTCCATCG
6051  GCTCCTCGAA GACGATCACC TCCCCTTTCT ACGGCGACAA GTCCACCGAG
6101  CCCGTCCAGA AGCTGTCCTT CGACGGCCAG AAGGTCTACC GCACCATCGC
6151  CAACACCGAC GTCGCGGCTT GGCCGAACGG CAAGGTCTAC CTGGGCGTCA
6201  CGAAGGTCGA CTTCTCCCAG TACGATGACC AGAAGAACGA GACCTCCACC
6251  CAGACCTACG ACTCCAAGCG CAACAATGGC CACGTCTCCG CCCAGGACTC
6301  CATCGACCAG CTGCCGCCTG AGACCACTGA CGAGCCCCTG GAGAAGGCCT
6351  ACTCCCACCA GCTGAACTAC GCGGAGTGCT TCCTGATGCA AGACCGCAGG
6401  GGCACCATCC CCTTCTTCAC CTGGACCCAC CGCTCCGTCG ACTTCTTCAA
6451  CACCATCGAC GCCGAGAAGA TCACCCAGCT GCCCGTGGTC AAGGCCTACG
6501  CCCTGTCCTC GGGTGCCTCC ATCATTGAGG GTCCAGGCTT CACCGGTGGC
6551  AACCTGCTGT TCCTGAAGGA GTCCTCGAAC TCCATCGCCA AGTTCAAGGT
6601  CACCCTGAAC TCCGCTGCCT TGCTGCAACG CTACCGCGTC CGCATCCGCT
6651  ACGCCTCCAC CACGAACCTG CGCCTGTTCG TCCAGAACTC CAACAATGAC
6701  TTCCTGGTCA TCTACATCAA CAAGACCATG AACAAGGACG ATGACCTGAC
6751  CTACCAGACC TTCGACCTCG CCACCACGAA CTCCAACATG GGCTTCTCGG
6801  GCGACAAGAA TGAACTGATC ATTGGTGCTG AGTCCTTCGT CTCCAACGAG
6851  AAGATCTACA TCGACAAGAT CGAGTTCATC CCCGTCCAGC TGTGATAGGA
6901  ACTCTGATTG AATTCTGCAT GCGTTTGGAC GTATGCTCAT TCAGGTTGGA
6951  GCCAATTTGG TTGATGTGTG TGCGAGTTCT TGCGAGTCTG ATGAGACATC
7001  TCTGTATTGT GTTTCTTTCC CCAGTGTTTT CTGTACTTGT GTAATCGGCT
7051  AATCGCCAAC AGATTCGGCG ATGAATAAAT GAGAAATAAA TTGTTCTGAT
7101  TTTGAGTGCA AAAAAAAAGG AATTAGATCT GTGTGTGTTT TTTGGATCCC
7151  CGGGGCGGCC GCTCGAGCAG GACCTGCAGA AGCTAGCTTG ATGGGGATCA
7201  GATTGTCGTT TCCCGCCTTC AGTTTAAACA GAGTCGGGTT TGGATGGTCA
7251  ACTCCGGCAT ACTGCCGAAA ACAAACCAAT CCGTCACCGT CAAGGCCCCG
7301  CACCGCTGGC CGCACGCAGG AAAAATAAGT TGCGACCGCG AGCGGGCGAA
7351  TCAGAAAGGG CGTCCGGCCT TGGTCAGACA CGACAGCGAC GCGGAAAGGC
7401  TGCGCCCGCG GTGCCATCTA CAAGGGTCCA CGTCCATCCA AAAAGAGCGG
```

CORN PLANT MON88017 AND COMPOSITIONS AND METHODS FOR DETECTION THEREOF

CROSS-REFERENCE TO RELATED APPLICATIONS

This application is a divisional of U.S. patent application Ser. No. 10/582,007, filed Aug. 17, 2007 now U.S. Pat. No. 8,212,113; which is the 371 National Stage application of International Application No. PCT/US2004/041723, filed Dec. 14, 2004; which claims the benefit of U.S. Provisional Application No. 60/529,477, filed Dec. 15, 2003, all of which are incorporated herein by reference in their entireties including their respective sequence listings.

FIELD OF THE INVENTION

The present invention relates to the field of plant molecular biology. More specifically, the invention relates to a glyphosate tolerant and insect resistant corn plant MON88017 and to assays and methods for detecting the presence of corn plant MON88017 DNA in a plant sample and compositions thereof.

DESCRIPTION OF THE RELATED ART

Corn is an important crop and is a primary food source in many areas of the world. The methods of biotechnology have been applied to corn for improvement of the agronomic traits and the quality of the product. One such agronomic trait is herbicide tolerance, in particular, tolerance to glyphosate herbicide. This trait in corn has been conferred by the expression of a transgene in the corn plant that expresses a glyphosate resistant 5-enolpyruvyl-3-phosphoshikimate synthase (CP4 EPSPS, U.S. Pat. No. 5,633,435). Another agronomic trait is insect resistance, for example genetically engineered corn plant resistance to the corn borer and the corn rootworm (U.S. Pat. No. 6,489,542 and U.S. Pat. No. 6,620,988). It would be advantageous to be able to detect the presence of transgene/genomic DNA of a particular plant in order to determine whether progeny of a sexual cross contain the transgene/genomic DNA of interest. In addition, a method for detecting a particular plant would be helpful when complying with regulations requiring the pre-market approval and labeling of foods derived from the recombinant crop plants.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al., Ann. Rev. Genet 22:421-477, 1988). For this reason, it is often necessary to screen a large number of plants in order to identify a plant characterized by optimal expression of an introduced gene of interest. For example, it has been observed in plants and in other organisms that there may be a wide variation in levels of expression of an introduced transgene among plants. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce hundreds to thousands of different transgenic plants and screen those plants for a single plant that has desired transgene expression levels and phenotype for commercial purposes. A plant that has desired levels or patterns of transgene expression is useful for introgressing the transgene into other genetic backgrounds by sexual crossing using conventional breeding methods. Progeny of such crosses maintain the transgene expression characteristics of the original transformant. This strategy is used to ensure reliable gene expression in a number of varieties that are well adapted to local growing conditions and market demands.

It is possible to detect the presence of a transgene by any well-known nucleic acid detection methods such as the polymerase chain reaction (PCR) or DNA hybridization using polynucleic acid probes. These detection methods generally use DNA primer or probe molecules that are specific to the genetic elements, such as promoters, leaders, introns, coding regions, 3' transcription terminators, marker genes, etc, that are the components of the transgenes of a DNA construct. As a result, such methods may not be useful for discriminating between different transgenic events, particularly those produced using the same transgene DNA construct unless the sequence of genomic DNA adjacent to the inserted transgene DNA is known. Event-specific DNA detection methods have been developed for many transgenic crop plant introductions, for example sugar beet (U.S. Pat. No. 6,531,649), wheat (US patent pub 20020062503), insect resistant corn (US patent pub 20020102582), and a glyphosate tolerant corn event nk603 (US patent pub 20020013960).

The present invention relates to a glyphosate tolerant and corn rootworm resistant corn plant MON88017, and compositions contained therein, and to the method for the detection of the transgene/genomic insertion region in corn plant MON88017 and progeny thereof containing these compositions.

SUMMARY OF THE INVENTION

The present invention is related to the transgenic corn plant designated MON88017 having seed deposited with American Type Culture Collection (ATCC) with Accession No. PTA-5582. Another aspect of the invention comprises the progeny plants, or seeds, or regenerable parts of the plants and seeds of the plant MON88017. The invention also includes plant parts of corn plant MON88017 that include, but are not limited to pollen, ovule, seed, roots, and leaves. The invention relates to a corn plant MON88017 having a glyphosate tolerant phenotype and a corn rootworm resistant phenotype and the novel genetic compositions contained in the genome of MON88017.

One aspect of the invention provides DNA compositions and methods for detecting the presence of a transgene/genomic junction region from corn plant MON88017. Isolated DNA molecules are provided that comprise at least one transgene/genomic junction DNA molecule selected from the group consisting of SEQ ID NO:1 and SEQ ID NO:2, and complements thereof, wherein the junction molecule spans the transgene insertion site, which comprises a heterologous DNA inserted into the corn genome and corn genomic DNA flanking the insertion site in corn plant MON88017. A corn seed and plant material thereof comprising any one of these DNA molecules is an aspect of this invention.

An isolated DNA molecule is provided that is a transgene/genomic region SEQ ID NO:3 or the complement thereof, wherein this DNA molecule is novel in the genome of corn plant MON88017. A corn plant and seed comprising SEQ ID NO:3 in its genome is an aspect of this invention.

According to another aspect of the invention, an isolated DNA molecule is provided that is a transgene/genomic region SEQ ID NO:4, or the complement thereof, wherein this DNA molecule is novel in the genome of corn plant MON88017. A corn plant and seed comprising SEQ ID NO:4 in its genome is an aspect of this invention.

An isolated DNA molecule is provided that is a transgene/genomic region, SEQ ID NO:5 of MON88017 or the complement thereof, wherein this DNA molecule is novel in the genome of corn plant MON88017. A corn plant and seed comprising SEQ ID NO:5 in its genome is an aspect of this invention.

According to another aspect of the invention, two DNA molecules comprising a primer pair are provided for use in a DNA detection method, wherein the first DNA molecule comprises at least 11 or more contiguous polynucleotides of any portion of the transgene DNA region of the DNA molecule of SEQ ID NO:3 or the complement thereof, and a second DNA molecule comprising at least 11 or more contiguous polynucleotides of any portion of a corn genomic DNA region of SEQ ID NO:3 or complement thereof, wherein these DNA molecules when used together comprise a DNA primer set in a DNA amplification method that produces an amplicon. The amplicon produced using the DNA primer pair in the DNA amplification method is diagnostic for corn plant MON88017 when the amplicon contains SEQ ID NO:1. Any length amplicon produced from MON88017 DNA wherein the amplicon comprises SEQ ID NO:1 is an aspect of the invention. The skilled artisan will recognize that the first and second DNA molecules are not required to consist only of DNA but may also be comprised exclusively of RNA, a mixture of DNA and RNA, or a combination of DNA, RNA, or other nucleotides or analogues thereof that do not act as templates for one or more polymerases. In addition, the skilled artisan will recognize that a probe or a primer as set forth herein shall be at least from about 11, 12, 13, 14, 15, 16, 17, 18, 19, and 20 consecutive nucleotides in length and selected from the group of nucleotides as set forth in SEQ ID NO:1 (arbitrarily designated 5' junction), SEQ ID NO:2 (arbitrarily designated 3' junction), SEQ ID NO:3 (portion of the arbitrarily designated 5' flanking sequence), SEQ ID NO:4 (portion of the arbitrarily designated 3' flanking sequence), and SEQ ID NO:5 (all or a portion of the inserted nucleotide sequence). Probes and primers at least from about 21 to about 50 or more consecutive nucleotides in length are possible when selected from the group of nucleotides as set forth in SEQ ID NO:3, SEQ ID NO:4, and SEQ ID NO:5.

According to another aspect of the invention, two DNA molecules comprising a primer pair are provided for use in a DNA detection method, wherein the first DNA molecule comprises at least 11 or more contiguous polynucleotides of any portion of the transgene DNA region of the DNA molecule of SEQ ID NO:4 or the complement thereof, and a second DNA molecule comprising at least 11 or more contiguous polynucleotides of any portion of a corn genomic DNA region of SEQ ID NO:4 or complement thereof, wherein these DNA molecules when used together comprise a DNA primer set in a DNA amplification method that produces an amplicon. The amplicon produced using the DNA primer pair in the DNA amplification method is diagnostic for corn plant MON88017 when it comprises SEQ ID NO:2. Any length amplicon produced from MON88017 DNA, wherein the amplicon comprises SEQ ID NO:2 is an aspect of the invention.

According to another aspect of the invention, methods of detecting the presence of DNA corresponding specifically to the corn plant MON88017 DNA in a sample are provided. Such methods comprise: (a) contacting the sample comprising MON88017 genomic DNA with a DNA primer pair; and (b) performing a nucleic acid amplification reaction, thereby producing an amplicon; and (c) detecting the amplicon, wherein the amplicon comprises SEQ ID NO:1 or SEQ ID NO:2.

According to another aspect of the invention, methods of detecting the presence of DNA corresponding specifically to the corn plant MON88017 DNA in a sample are provided. Such methods comprising: (a) contacting the sample comprising MON88017 DNA with a DNA probe comprising SEQ ID NO:1 or SEQ ID NO:2, or DNA molecules substantially homologous to SEQ ID NO:1 or SEQ ID NO:2 that hybridize under stringent hybridization conditions with genomic DNA from corn plant MON88017 and does not hybridize under the stringent hybridization conditions with non-MON88017 corn plant DNA; (b) subjecting the sample and probe to stringent hybridization conditions; and (c) detecting hybridization of the probe to the corn plant MON88017 DNA.

According to another aspect of the invention, methods of producing a corn plant that tolerates application of glyphosate and are resistant to corn rootworm are provided that comprise the step of: sexually crossing a first parental corn plant MON88017 with a second parental corn plant that lacks the glyphosate tolerance and corn rootworm resistance, thereby producing hybrid progeny plants that are glyphosate tolerant and corn rootworm resistant.

In another aspect of the invention is a method of determining the zygosity of the progeny of corn event MON88017 comprising: (a) contacting the sample comprising corn DNA with a primer set comprising SEQ ID NO:32, SEQ ID NO:33 and SEQ ID NO:34, that when used in a nucleic-acid amplification reaction with genomic DNA from corn event MON88017, produces a first amplicon that is diagnostic for corn event MON88017; and (b) performing a nucleic acid amplification reaction, thereby producing the first amplicon; and (c) detecting the first amplicon; and (d) contacting the sample comprising corn DNA with said primer set, that when used in a nucleic-acid amplification reaction with genomic DNA from corn plants produces a second amplicon comprising the native corn genomic DNA homologous to the corn genomic region of a transgene insertion identified as corn event MON88017; and (e) performing a nucleic acid amplification reaction, thereby producing the second amplicon; and (f) detecting the second amplicon; and (g) comparing the first and second amplicons in a sample, wherein the presence of both amplicons indicates the sample is heterozygous for the transgene insertion.

A method for controlling weeds in a field of corn plant MON88017 comprising the step of applying an effective amount of glyphosate containing herbicide to the field of MON88017 corn plants.

A hybrid corn seed comprising wherein at least one parent is MON88017.

A corn plant transformed with a plant DNA construct comprising the plant expression cassettes of pMON53616.

The foregoing and other aspects of the invention will become more apparent from the following detailed description and accompanying drawings.

BRIEF DESCRIPTION OF THE DRAWINGS

FIG. 3. MON88017 5' transgene/genomic DNA region (SEQ ID NO:3).
FIG. 4. MON88017 3' transgene/genomic DNA region (SEQ ID NO:4).
FIG. 5. MON88017 transgene/genomic DNA region (SEQ ID NO:5)

DETAILED DESCRIPTION OF THE PREFERRED EMBODIMENTS

A transgenic corn plant, herein referred to as "plant MON88017" or "MON88017", is resistant to feeding damage by the Coleopteran pest corn rootworm (*Diabrotica* spp.), and is tolerant to the phytotoxic action of glyphosate containing agricultural herbicides. This dual-trait corn plant expresses a modified variant of the CRY3Bb1 protein (U.S. Pat. No. 6,501,009) from *Bacillus thuringiensis* (subsp. *kumamotoensis*), that provides resistance to feeding damage by corn rootworm larvae, and a glyphosate resistant 5-enolpyruvylshikimate-3-phosphate synthase (CP4 EPSPS) protein (U.S. Pat. No. 5,633,435) from *Agrobacterium* sp. strain CP4 that confers plant tolerance to glyphosate. Use of the dual-trait corn will provide major benefits to corn growers: a) protection from economic losses due to the corn rootworm larvae, a major insect pest in the U.S. and growing concern in many corn growing areas of the world, and b) the ability to apply glyphosate containing agricultural herbicides to the corn crop for broad-spectrum weed control. Additionally, the transgenes encoding the corn rootworm and glyphosate tolerant traits are linked on the same DNA segment and occur at a single locus in the genome of MON88017, this provides for enhanced breeding efficiency and enables the use of molecular markers to track the transgene insert in the breeding populations and progeny thereof.

Figure 1:
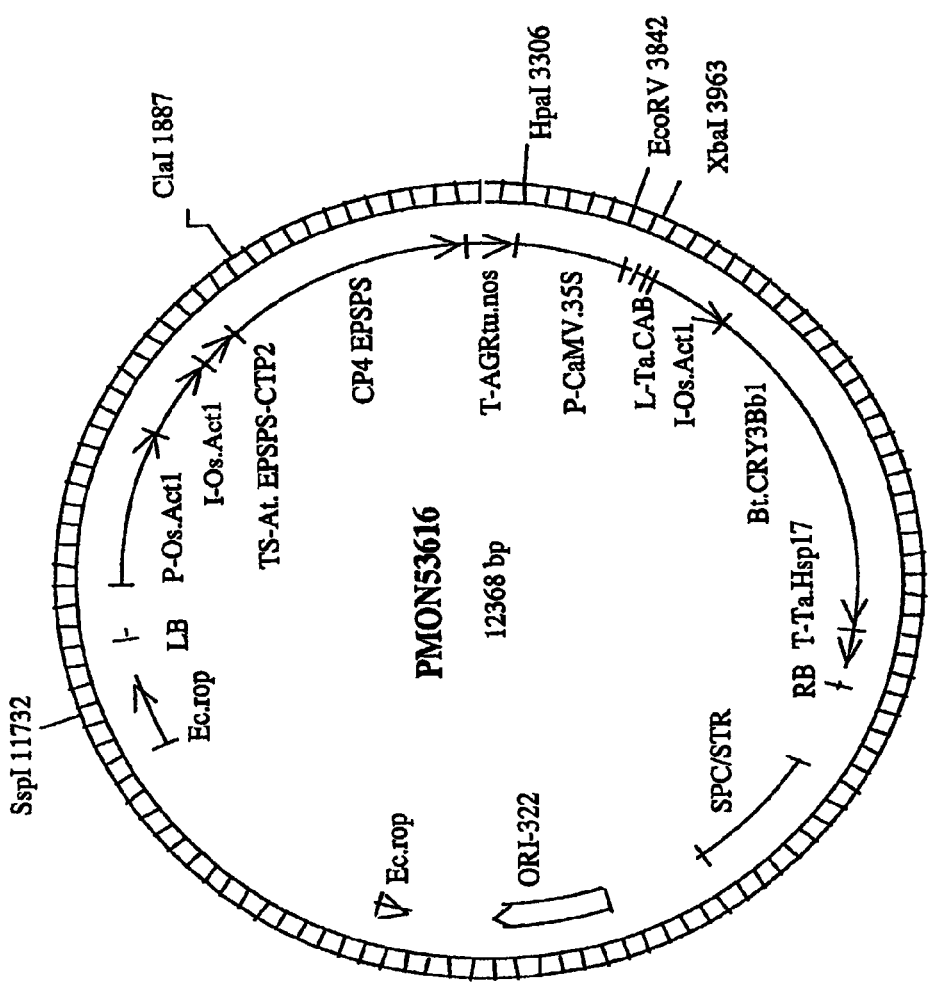
FIG. 1. Plasmid map of pMON53616.

The corn plant MON88017 was produced by an *Agrobacterium* mediated transformation process of an inbred corn line with the plasmid construct pMON53616 (FIG. 1). This plasmid construct contains the linked plant expression cassettes with the regulatory genetic elements necessary for expression of the CRY3Bb1 protein and the CP4 EPSPS protein in corn plant cells. Corn cells were regenerated into intact corn plants and individual plants were selected from the population of plants that showed integrity of the plant expression cassettes and resistance to glyphosate and corn rootworm larvae feeding damage. A corn plant that contains in its genome the linked plant expression cassettes of pMON53616 is an aspect of the present invention.

The plasmid DNA inserted into the genome of corn plant MON88017 was characterized by detailed molecular analyses. These analyses included: the insert number (number of integration sites within the corn genome), the copy number (the number of copies of the T-DNA within one locus), and the integrity of the inserted gene cassettes. DNA molecular probes were used that included the intact CP4 EPSPS and CRY3Bb1 coding regions and their respective regulatory elements, the promoters, introns, and polyadenylation sequences of the plant expression cassettes, and the plasmid pMON53616 backbone DNA region. The data show that MON88017 contains a single T-DNA insertion with one copy of both the CRY3Bb1 and the CP4 EPSPS cassettes. No additional elements from the transformation vector pMON53616, linked or unlinked to intact gene cassettes, were detected in the genome of MON88017. Finally, PCR and DNA sequence analyses were performed to determine the 5' and 3' insert-to-plant genome junctions, confirm the organization of the elements within the insert (FIG. 2), and determine the complete DNA sequence of the insert in corn plant MON88017 (SEQ ID NO:5).

A glyphosate tolerant, corn rootworm resistant corn plant can be bred by first sexually crossing a first parental corn plant, consisting of a corn plant grown from MON88017, with a second parental corn plant that lacks the tolerance to glyphosate herbicide, thereby producing a plurality of hybrid progeny plants. Inbred corn lines can be generated by a process that includes, backcrossing with the recurrent parent, and selection with glyphosate treatment. Descriptions of other breeding methods that are commonly used for different traits and crops can be found in references known in the art, e.g., Fehr, in *Breeding Methods for Cultivar Development*, Wilcox J. ed., American Society of Agronomy, Madison Wis. (1987).

Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR §1.822 is used.

As used herein, the term "corn" means *Zea mays* and includes all plant varieties that can be bred with corn plant MON88017.

As used herein, the term "comprising" means "including but not limited to".

"Glyphosate" refers to N-phosphonomethylglycine and its salts. N-phosphonomethylglycine is a well-known herbicide that has activity on a broad spectrum of plant species. Glyphosate is the active ingredient of Roundup® (Monsanto Co.), a safe herbicide having a desirably short half-life in the environment. Glyphosate is the active ingredient of Roundup® herbicide (Monsanto Co.). Treatments with "glyphosate herbicide" refer to treatments with the Roundup®, Roundup Ultra®, Roundup Pro® herbicide or any other herbicide formulation containing glyphosate. Examples of commercial formulations of glyphosate include, without restriction, those sold by Monsanto Company as ROUNDUP®, ROUNDUP® ULTRA, ROUNDUP® ULTRAMAX, ROUNDUP® WEATHERMAX, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Syngenta Crop Protection as TOUCHDOWN® herbicide, which contains glyphosate as its trimethylsulfonium salt. When applied to a plant surface, glyphosate moves systemically through the plant. Glyphosate is phytotoxic due to its inhibition of the shikimic acid pathway, which provides a precursor for the synthesis of aromatic amino acids. Glyphosate inhibits the enzyme 5-enolpyruvyl-3-phosphoshikimate synthase (EPSPS) found in plants. Glyphosate tolerance can be achieved by the expression of bacterial EPSPS variants and plant EPSPS variants that have lower affinity for glyphosate and therefore retain their catalytic activity in the presence of glyphosate (U.S. Pat. Nos. 5,633,435, 5,094,945, 4,535,060, and 6,040,497).

Corn rootworm (CRW, *Diabrotica* spp) larvae feed on the roots of developing corn plants. Substantial expense and time is devoted to controlling the economic damage caused by this pest. Chemical insecticides, including organophosphates, carbamates and pyrethroids are incorporated into the soil on over 16 million corn acres annually to control CRW. The benefits of shifting away from soil insecticides to a transgenic approach are impressive and include a reduction in potential human health and safety risks, reduced direct impacts on nontarget organisms, reduced contamination of surface and ground water supplies, decreased pesticide container disposal problems, and general compatibility with other pest management and agronomic programs.

The present invention provides for transgenic plants which have been transformed with a DNA construct that contains at least one expression cassette that expresses high levels of CRY3Bb1 delta-endotoxin and at least one expression cassette that expresses a glyphosate tolerance enzyme. Corn plants transformed according to the methods and with the DNA construct disclosed herein are resistant to CRW. The same corn plants are also resistant to glyphosate herbicide. The linked agronomic traits provide ease in maintaining these traits together in a breeding population.

A transgenic "plant" is produced by transformation of a plant cell with heterologous DNA, i.e., a polynucleic acid construct that includes a transgene of interest; regeneration of a population of plants resulting from the insertion of the transgene into the genome of the plant cell, and selection of a particular plant characterized by insertion into a particular genome location. The term "event" refers to the original transformant plant and progeny of the transformant that include the heterologous DNA. The term "event" also includes progeny produced by a sexual outcross between the event and another plant wherein the progeny includes the heterologous DNA. Even after repeated back-crossing to a recurrent parent, the inserted DNA and flanking genomic DNA from the transformed parent event is present in the progeny of the cross at the same chromosomal location. The term "event" also refers to DNA from the original transformant comprising the inserted DNA, and flanking genomic sequence immediately adjacent to the inserted DNA, that would be expected to be transferred to a progeny that receives the inserted DNA including the transgene of interest as the result of a sexual cross of one parental line that includes the inserted DNA (e.g., the original transformant and progeny resulting from selfing) and a parental line that does not contain the inserted DNA. The present invention is related to the transgenic event, corn plant MON88017, progeny thereof, and DNA compositions contained therein.

A "probe" is an isolated nucleic acid to which is attached a conventional detectable label or reporter molecule, e.g., a radioactive isotope, ligand, chemiluminescent agent, or enzyme. Such a probe is complementary to a strand of a target nucleic acid, in the case of the present invention, to a strand of genomic DNA from MON88017 whether from a MON88017 plant or from a sample that includes MON88017 DNA. Probes according to the present invention include not only deoxyribonucleic or ribonucleic acids, but also polyamides and other probe materials that bind specifically to a target DNA sequence and can be used to detect the presence of that target DNA sequence.

DNA primers are isolated polynucleic acids that are annealed to a complementary target DNA strand by nucleic acid hybridization to form a hybrid between the primer and the target DNA strand, then extended along the target DNA strand by a polymerase, e.g., a DNA polymerase. A DNA primer pair or a DNA primer set of the present invention refer to two DNA primers useful for amplification of a target nucleic add sequence, e.g., by the polymerase chain reaction (PCR) or other conventional polynucleic acid amplification methods.

DNA probes and DNA primers are generally 11 polynucleotides or more in length, often 18 polynucleotides or more, 24 polynucleotides or more, or 30 polynucleotides or more. Such probes and primers are selected to be of sufficient length to hybridize specifically to a target sequence under high stringency hybridization conditions. Preferably, probes and primers according to the present invention have complete sequence similarity with the target sequence, although probes differing from the target sequence that retain the ability to hybridize to target sequences may be designed by conventional methods.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR DNA primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking genomic DNA and insert sequences disclosed herein can be used to confirm (and, if necessary, to correct) the disclosed DNA sequences by conventional methods, e.g., by re-cloning and sequencing such DNA molecules.

The nucleic acid probes and primers of the present invention hybridize under stringent conditions to a target DNA molecule. Any conventional nucleic acid hybridization or amplification method can be used to identify the presence of DNA from a transgenic plant in a sample. Polynucleic acid molecules, also referred to as nucleic acid segments, or fragments thereof are capable of specifically hybridizing to other nucleic acid molecules under certain circumstances. As used herein, two polynucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. Appropriate stringency conditions that promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a polynucleic acid of the present invention will specifically hybridize to one or more of the nucleic acid molecules set forth in SEQ ID NOs: 1, 2, 3, 4, or 5, or complements thereof or fragments of either under moderately stringent conditions, for example at about 2.0× SSC and about 65° C. In a particularly preferred embodiment, a nucleic acid of the present invention will specifically hybridize to one or more of the nucleic acid molecules set forth in SEQ ID NOs: 1, 2, 3, 4, or 5 or complements or fragments of either under high stringency conditions. In one aspect of the present invention, a preferred marker nucleic acid molecule of the present invention has the nucleic acid sequence set forth in SEQ ID NO:1 or SEQ ID NO:2 or complements thereof or fragments of either. In another aspect of the present invention, a preferred marker nucleic acid molecule of the present invention shares between 80% and 100% or 90% and 100% sequence identity with the nucleic acid sequence set forth in SEQ ID NO:1 or SEQ ID NO:2 or complement thereof or fragments of either. In a further aspect of the present invention, a preferred marker nucleic acid molecule of the present invention shares between 95% and 100% sequence identity with the sequence set forth in SEQ ID NO:1 or SEQ ID NO:2 or complement thereof or fragments of either. SEQ ID NO:1 or SEQ ID NO:2 may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of polynucleic acid amplification method directed to a target polynucleic acid molecule that is part of a polynucleic acid template. For example, to determine whether a corn plant resulting from a sexual cross contains transgenic plant genomic DNA from the corn plant MON88017 plant of the present invention, DNA that is extracted from a corn plant tissue sample may be subjected to a polynucleic acid amplification method using a primer pair that includes a primer derived from DNA sequence in the genome of the MON88017 plant adjacent to the insertion site of the inserted heterologous DNA (transgene DNA), and a second primer derived from the inserted heterologous DNA to produce an amplicon that is diagnostic for the presence of the MON88017 plant DNA. The diagnostic amplicon is of a length and has a DNA sequence that is also diagnostic for the plant genomic DNA, the DNA sequence of the amplicon comprising SEQ ID NO:1 or SEQ ID NO:2. The amplicon may range in length from the combined length of the primer pair plus one nucleotide base pair, preferably plus about fifty nucleotide base pairs, more preferably plus about two hundred-fifty nucleotide base pairs, and even more preferably plus about four hundred-fifty nucleotide base pairs or more. Alternatively, a primer pair can be derived from genomic sequence on both sides of the inserted heterologous DNA so as to produce an amplicon that includes the entire insert polynucleotide sequence (e.g., a forward primer isolated from the genomic portion of SEQ ID NO:3 and a reverse primer isolated from the genomic portion of SEQ ID NO:4 that amplifies a DNA molecule comprising the two expression cassettes of pMON53616 DNA fragment that was inserted into the MON88017 genome, the insert comprising about 7125 nucleotides of SEQ ID NO:5, FIG. 2 and FIG. 5). A member of a primer pair derived from the plant genomic sequence adjacent to the transgene insert DNA is located a distance from the inserted DNA sequence, this distance can range from one nucleotide base pair up to about twenty thousand nucleotide base pairs. The use of the term "amplicon" specifically excludes primer dimers that may be formed in the DNA thermal amplification reaction.

Polynucleic acid amplification can be accomplished by any of the various polynucleic acid amplification methods known in the art, including the polymerase, chain reaction (PCR). Amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb (kilobase) of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking genomic DNA sequence from MON88017 can be verified (and corrected if necessary) by amplifying such DNA molecules from the MON88017 seed or plants grown from the seed deposited with the ATCC having accession no. PTA-5582, using primers derived from the sequences provided herein, followed by standard DNA sequencing of the PCR amplicon or cloned DNA fragments thereof.

DNA detection kits that are based on DNA amplification methods contain DNA primer molecules that hybridize specifically to a target DNA and amplify a diagnostic amplicon under the appropriate reaction conditions. The kit may provide an agarose gel based detection method or any number of methods of detecting the diagnostic amplicon that are known in the art. A kit that contains DNA primers that are homologous or complementary to any portion of the corn genomic region of SEQ ID NO:3 or SEQ ID NO:4 and to any portion of the transgene insert region of SEQ ID NO:5 is an object of the invention. Specifically identified as a useful primer pair in a DNA amplification method is SEQ ID NO:6 and SEQ ID NO:7 that amplify a diagnostic amplicon homologous to a portion of the 5' transgene/genome region of MON88017, wherein the amplicon comprises SEQ ID NO:1. Other DNA molecules useful as DNA primers can be selected from the disclosed transgene/genomic DNA sequence of MON88017 (SEQ ID NO:5) by those skilled in the art of DNA amplification.

The diagnostic amplicon produced by these methods may be detected by a plurality of techniques. One such method is Genetic Bit Analysis (Nikiforov, et al. Nucleic Acid Res. 22:4167-4175, 1994) where a DNA oligonucleotide is designed that overlaps both the adjacent flanking genomic DNA sequence and the inserted DNA sequence. The oligonucleotide is immobilized in wells of a microtiter plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled dideoxynucleotide triphosphates (ddNTPs) specific for the expected next base. Readout may be fluorescent or ELISA-based. A signal indicates presence of the transgene/genomic sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene/genomic sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed that overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene/genomic sequence due to successful amplification, hybridization, and single base extension.

Taqman® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the transgene/genomic sequence due to successful amplification and hybridization.

Molecular Beacons have been described for use in sequence detection as described in Tyangi, et al. (Nature Biotech. 14:303-308, 1996) Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking/transgene insert sequence due to successful amplification and hybridization.

DNA detection kits can be developed using the compositions disclosed herein and the methods well known in the art of DNA detection. The kits are useful for identification of corn plant MON88017 DNA in a sample and can be applied to methods for breeding corn plants containing MON88017 DNA. A kit contains DNA molecules that are useful as primers or probes and that are homologous or complementary to at least a portion of SEQ ID NO:1, 2, 3, 4, or 5. The DNA molecules can be used in DNA amplification methods (PCR) or as probes in polynucleic acid hybridization methods, i.e., Southern analysis, northern analysis. The plasmid vector pMON53616 used to produce corn event MON88017 contains two expression cassettes: expression cassette one comprises the CaMV 35S promoter with duplicated enhancer linked to the wheat CAB 5' leader linked to the rice actin 1 intron linked to the CRY3Bb1 coding region linked to the wheat Hsp17 3' polyadenylation sequence; and linked to expression cassette two that comprises the rice actin 1 promoter linked to the rice actin 1 intron driving transcription of a chloroplast transit peptide fused to the CP4 EPSPS coding region and linked to the NOS 3' polyadenylation region, the sequence of the linked expression cassettes is contained in SEQ ID NO:5.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Figure 2:
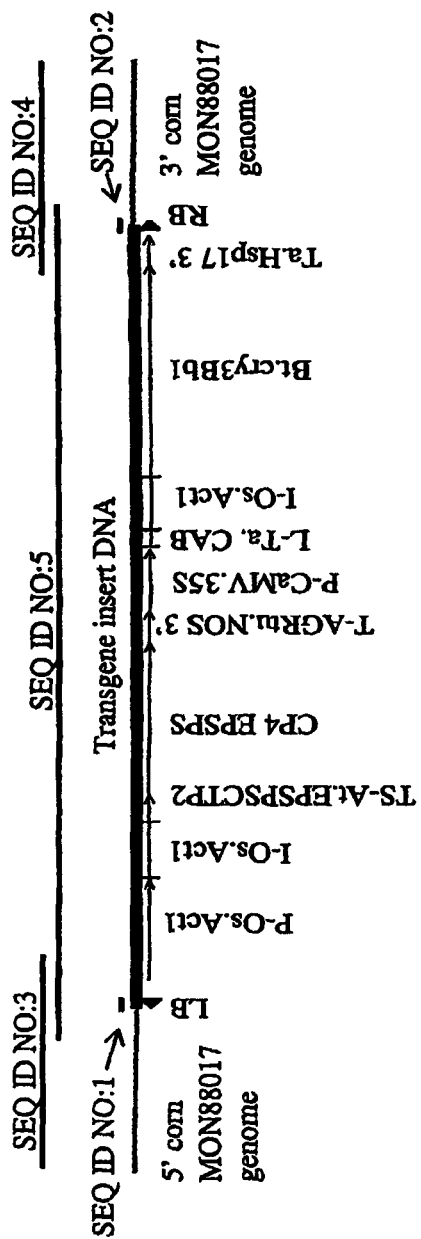
FIG. 2. Genomic organization of insert in corn plant MON88017.

The transgenic corn plant MON88017 was generated by an *Agrobacterium*-mediated transformation of corn cells with a DNA fragment derived from pMON53616 (FIG. 1). The plant transformation construct, pMON53616 was mated into *Agrobacterium* using a triparental mating procedure (Ditta et al., Proc. Natl. Acad. Sci. 77:7347-7351, 1980). The DNA fragment of pMON53616 that contains two transgene plant expression cassettes was inserted into the genome of a corn plant cell, the corn plant cell was regenerated into corn plant MON88017. The configuration of the insert into the genome of MON88017 is shown in (FIG. 2). MON88017 and it progeny have tolerance to glyphosate and are resistant to corn rootworm larvae feeding damage. Corn transformation was performed essentially as described herein.

Liquid cultures of *Agrobacterium* containing pMON53616 are initiated from glycerol stocks or from a freshly streaked plate and grown overnight at 26° C.-28° C. with shaking (approximately 150 revolutions per minute, rpm) to mid-log growth phase in liquid LB medium, pH 7.0, containing 50 mg/l (milligram per liter) kanamycin, and either 50 mg/l streptomycin or 50 mg/l spectinomycin, and 25 mg/l chloramphenicol with 200 μM acetosyringone (AS). The *Agrobacterium* cells are resuspended in the inoculation medium (liquid CM4C, as described in Table 8 of U.S. Pat. No. 6,573,361) and the cell density is adjusted such that the resuspended cells have an optical density of 1 when measured in a spectrophotometer at a wavelength of 660 nm (i.e., $OD_{660}$). Freshly isolated Type II immature Hill×LH198 and Hill corn embryos are inoculated with *Agrobacterium* and co-cultured 2-3 days in the dark at 23° C. The embryos are then transferred to delay media (N6 1-100-12; as described in Table 1 of U.S. Pat. No. 5,424,412) supplemented with 500 mg/l Carbenicillin (Sigma-Aldrich, St Louis, Mo.) and 20 μM $AgNO_3$) and incubated at 28° C. for 4 to 5 days. All subsequent cultures are kept at this temperature.

The corn coleoptiles are removed one week after inoculation. The embryos are transferred to the first selection medium (N61-0-12, as described in Table 1 of U.S. Pat. No. 5,424,412), supplemented with 500 mg/l Carbenicillin and 0.5 mM glyphosate. Two weeks later, surviving tissues are transferred to the second selection medium (N61-0-12) supplemented with 500 mg/l Carbenicillin and 1.0 mM glyphosate. Surviving callus is subcultured every 2 weeks for about 3 subcultures on 1.0 mM glyphosate. When glyphosate tolerant tissues are identified, the tissue is bulked up for regeneration. For regeneration, callus tissues are transferred to the regeneration medium (MSOD, as described in Table 1 of U.S. Pat. No. 5,424,412) supplemented with 0.1 μM abscisic acid (ABA; Sigma-Aldrich, St Louis, Mo.) and incubated for two weeks. The regenerating calli are transferred to a high sucrose medium and incubated for two weeks. The plantlets are transferred to MSOD media (without ABA) in a culture vessel and incubated for two weeks. Then the plants with roots are transferred into soil. Those skilled in the art of corn cell transformation methods can modify this method to provide transgenic corn plants containing the DNA construct of the present invention, or use other methods, such as, particle gun, that are known to provide transgenic monocot plants.

The MON88017 plant and seed has regenerable parts. The regenerable parts of the seed include, but are not limited to the embryo, the cotyledon, and the shoot or root meristem. The invention also includes plant parts of corn plant MON88017 that include, but are not limited to pollen, ovule, shoots, roots, and leaves. The invention also includes extractable components of MON88017 seed that include, but are not limited to protein, meal, flour, and oil.

Example 2

The corn plant MON88017 was selected from many transgenic corn plants for tolerance to glyphosate vegetative and reproductive injury. The successful production of a commercial quality transgenic plant currently requires producing a large number of transgenic plants. In the present invention, MON88017 was one plant among approximately 472 $R_0$ events that had been transformed with different DNA constructs that included pMON53616. The MON88017 event was selected from the many events by a series of molecular analysis, glyphosate tolerance screens, insect resistance screens, and expression analysis screens.

Transgenic corn plants were assayed for corn rootworm resistance to feeding damage by greenhouse and field screens. Root damage was rated using the Node-Injury Scale (NIS) developed by Oleson and Tollefson of Iowa State University, this scale rates damage done to corn roots using 0-3 values. The 0.00 value describes no feeding damage and is the lowest rating, 1.00 describes one node or the equivalent of an entire node eaten back to within approximately two inches of the stalk, 2.00 describes two complete nodes eaten, and 3.00 describes three or more nodes eaten and is the highest rating. Damage in between complete nodes eaten is noted as the percentage of the node missing, i.e., 1.50 describes 1½ nodes eaten, 0.25 describes ¼ of one node eaten. Field plots were artificially infested with corn rootworm larvae by applying 1500-2000 eggs per linear foot of row at the V3-V4 growth stage. Insecticide treated rows were treated with Tefluthrin insecticide (Force® 3G, Zeneca Ag Products) at a rate of 5 ounces per 1000 feet of row. MON88017 demonstrated a root damage rating (RDR) of between 0.08 and 0.11 in multiple tests. The non-insecticide treated isoline showed an average RDR of 1.28. Insecticide treated non-insecticidal protein containing corn plants showed an average RDR of 0.44.

The transgenic corn plants were treated with glyphosate herbicide to determine the level of tolerance to the herbicide. Test plots were sprayed with glyphosate (Roundup® WeatherMax, Monsanto Co, St Louis, Mo.) that was applied twice during the growing season once at the V4 and once at the V8 growth stage at a rate of 1.125 and 2.25 pounds active ingredient per acre. The yield in corn seed was measured at harvest as percent yield relative to unsprayed (WeatherMax O) MON88017 plots. The results shown in Table 1 demonstrate that MON88017 is highly tolerant to glyphosate and were not reduced in yield, surprisingly the treated plots averaged higher in yield that the treated plots.

TABLE 1

Percent Yield of MON88017 treated with glyphosate compared to untreated

| Treatment | Replications | | | | | Average |
|---|---|---|---|---|---|---|
| WeatherMax 0 - V4 | 100.0 | 100.0 | 100.0 | 100.0 | 100.0 | 100.0 |
| WeatherMax 1.125 + 1.125 - V4/V8 | 99.2 | 118.5 | 102.1 | 100.4 | 107.7 | 105.1 |
| WeatherMax 2.25 + 2.25 - V4/V8 | 99.5 | 118.8 | 107.0 | 97.4 | 115.5 | 105.7 |

Table 1 Legend: Percent yield for each WeatherMax treatment at leaf stages from V4 to V8 were compared to percent yield for WeatherMax treatments at leaf stages from 0 to V4, with results of 0-V4 treatments establishing the 100 percent yield baseline for each treatment repetition.

Example 3

Genomic DNA from MON88017 and control substances was extracted from corn grain by first processing the grain to a fine powder. Approximately 6 grams of the processed grain were transferred to a 50 ml (milliliter) conical tube, then ~16 ml of CTAB extraction buffer [1.5% (w/v) CTAB, 75 mM Tris-HCl pH 8.0, 100 mM EDTA pH 8.0, 1.05 M NaCl, and 0.75% (w/v) PVP (MW 40,000)] and 8 microliter of RNase (10 mg/ml, Roche) were added to the processed grain. The samples were incubated at 65° C. for 30-60 minutes with intermittent mixing and then allowed to cool to room temperature. Approximately 15 ml of chloroform:isoamyl alcohol (24:1 (v/v)) was added to the samples. The suspension was mixed for 5 minutes and the two phases separated by centrifugation at ~16,000×g for 5 minutes at room temperature. The aqueous (upper) layer was transferred to a clean 50 ml conical tube. Approximately ¹⁄₁₀ volume (~1.5 ml) of 10% CTAB buffer [10% (w/v) CTAB and 0.7 M NaCl] and an equal volume of chloroform:isoamyl alcohol [24:1 (v/v)] was added to the aqueous phase, which was then mixed for 5 minutes. The samples were centrifuged at ~16,000×g for 5 minutes to separate the phases. The aqueous (upper) layer was removed, mixed with an equal volume (~15 ml) of CTAB precipitation buffer [1% (w/v) CTAB, 50 mM Tris pH 8.0, and 10 mM EDTA pH 8.0] and allowed to stand at room temperature for 1-2 hours. The samples were centrifuged at ~10,000×g for 10 minutes at room temperature to pellet the DNA. The supernatant was discarded, and the pellet was dissolved in approximately 2 ml of high salt TE buffer (10 mM Tris-HCl pH 8.0, 10 mM EDTA pH 8.0, and 1 M NaCl). Gentle swirling at 37° C. was performed to aid in dissolution of the pellet. If necessary, samples were centrifuged at ~23,000×g at room temperature for 2 minutes to pellet and remove debris. Approximately ⅟₁₀ volume (~150 µl) of 3 M NaOAc (pH 5.2) and 2 volumes (~4 ml relative to the supernatant) of chilled 100% ethanol were added to precipitate the DNA. The precipitated DNA was spooled into a microcentrifuge tube containing 70% ethanol. The DNA was pelleted in a microcentrifuge at maximum speed (~14,000 rpm) for ~5 minutes, vacuum-dried, and re-dissolved in TE buffer (pH 8.0). The DNA was then stored in a 4° C. refrigerator.

Ten µg of genomic DNA was digested with a selected restriction enzyme, e.g., SspI, EcoRV, ScaI, and SmaI, in 200 µl enzyme restriction buffer at 37° C. for more than 4 hours, and then inactivate enzyme at 70-80° C. for 15 minutes. DNA was extracted with Phenol and chloroform, and precipitated with EtOH, and dissolved in 200 µl. The DNA was then self-ligated in 1 ml ligation buffer and T4 DNA ligase at 4° C. for overnight. The ligation reaction was inactivated at 70-80° C. for 15 minutes, and precipitated with EtOH, and dissolved in 200 µl. The DNA was then used as template for PCR with specific primers within the CP4 EPSPS or CRY3Bb coding regions using High Fidelity Expand System (Roche), following the protocol provided by the Manufacture. A secondary PCR with nested primers were used for specific amplification. The PCR product was then cloned for sequencing analysis. A Universal GenomeWalker kit (cat #K1807-1, Clonetech, Palo Alto, Calif.) was used for isolation of the 5' and 3' transgene/genomic region DNA using adapter primers AP1 and AP2 included therein and the protocol provided by the manufacture.

The 5' (SEQ ID NO:3, FIG. 3) and 3' (SEQ ID NO:4, FIG. 4) transgene/genomic region DNA are isolated from the MON88017 genomic DNA utilizing PCR. Total genomic DNA (~10 µg) is digested with the restriction enzymes. The QIAquick PCR Purification columns are used to purify the DNA after digesting overnight at 37° C. The DNA is eluted from the columns with 50 µl of water and then diluted to 1 ml. The diluted eluate (85 µl) is combined with 10 µl of buffer (10×) and 5 µl of T4 Ligase to circularize the fragments. After an overnight incubation at 16° C., the ligase is heat inactivated at 70° C. The samples are amplified by PCR with a series of nested primers. The primer combinations for isolation of the 3' transgene/genome region included SEQ ID NO:8, SEQ ID NO:9, and AP1 as primary primers, SEQ ID NO:10 and AP2 as the secondary primers, and SEQ ID NO:11 for use as a sequencing primer; the isolation of the 5' transgene/genome region included SEQ ID NO:12, SEQ ID NO:14 and AP1 as primary primers, SEQ ID NO:13, SEQ ID NO:15 and AP2 as secondary primers.

The conditions for the PCR include: primary PCR=7 cycles of 94° C. for 2 seconds, 72° C. for 10 minutes; 37 cycles of 94° C. for 2 seconds, 67° C. for 10 minutes; 1 cycle of 67° C. for 10 minutes; secondary and tertiary PCR=5 cycles of 94° C. for 2 seconds, 72° C. for 10 minutes; 24 cycles of 94° C. for 2 seconds, 67° C. for 10 minutes; 1 cycle of 67° C. for 10 minutes.

Alternatively, DNA amplification by PCR of the 5' and 3' transgene/genome insert regions of the MON88017 event can be performed with conditions that include: 7 cycles of 94° C. for 25 seconds, 72° C. for 3 minutes; 37 cycles of 94° C. for 25 seconds, 67° C. for 3 minutes; 1 cycle of 67° C. for 7 minutes. All subsequent amplifications conducted with the following conditions: 7 cycles of 94° C. for 2 seconds, 72° C. for 4 minutes; 37 cycles of 94° C. for 2 seconds, 67° C. for 4 minutes; 1 cycle of 67° C. for 7 minutes. All amplicons are visualized on 0.8% agarose gels stained with ethidium bromide. The DNA is prepared for sequencing either by purifying the PCR samples directly with the QIAquick PCR Purification kit (cat #28104, Qiagen Inc., Valencia, Calif.) or by extracting the appropriate fragment from the gel and using the QIAquick Gel Extraction kit (cat #28704, Qiagen Inc.). The DNA fragments from the flanking regions of MON88017 transgene/genomic insert were subcloned using a TOPO TA Cloning® kit (Invitrogen, Carlsbad, Calif.). The DNA sequence of the 5' transgene/genomic region is shown in FIG. 3, the DNA sequence of the 3' transgene/genomic region is shown in FIG. 4 and the complete transgene insert and linked flanking genomic DNA is shown in FIG. 5.

The full-length transgene/genomic insert sequence (SEQ ID NO:5, FIG. 5) was isolated from MON88017 genomic DNA by overlapping PCR products. A series of DNA primers were designed to produce amplicons that contain DNA fragments of the transgene insert and a portion of the adjacent flanking genomic regions from the MON88017 genome. The DNA fragments were sequenced, the sequences were combined to create a contig of the fragment sequences that is SEQ ID NO:5 of the present invention. The DNA primer pair combinations were: SEQ ID NO:16 and SEQ ID NO:17, SEQ ID NO:18 and SEQ ID NO:17, SEQ ID NO:19 and SEQ ID NO:20, SEQ ID NO:21 and SEQ ID NO:22, SEQ ID NO:23 and SEQ ID NO:24, SEQ ID NO:25 and SEQ ID NO:26, SEQ ID NO:25 and SEQ ID NO:27. Total genomic DNA was used for all PCR reactions. All amplicons were visualized on 0.8% agarose gels stained with ethidium bromide. The DNA was prepared for sequencing either by purifying the PCR samples directly with the QIAquick PCR Purification kit or by extracting the appropriate fragment from the gel and using the QIAquick Gel Extraction kit. The DNA sequence was produced using DNA sequence analysis equipment (ABI Prism™ 377, PE Biosystems, Foster City, Calif.) and DNASTAR sequence analysis software (DNASTAR Inc., Madison, Wis.).

Example 4

DNA event primer pairs are used to produce an amplicon diagnostic for corn event MON88017. An amplicon diagnostic for MON88017 comprise at least one junction sequence, SEQ ID NO:1 or SEQ ID NO:2. Event primer pairs that will produce a diagnostic amplicon for MON88017, in which the primer pairs include, but are not limited to SEQ ID NO:6 and SEQ ID NO:7 for the 5' amplicon sequence as outlined in Table 2. The location of primer SEQ ID NO:6 is in the corn genome as shown in FIG. 3 beginning at nucleotide position 952. The location of primer SEQ ID NO:7 is in the transgene insert as shown in FIG. 5 beginning at nucleotide position 450. The expected amplicon size using SEQ ID NO:6 and SEQ ID NO:7 in a DNA amplification method with MON88017 DNA is approximately 550 bps. In addition to these primer pairs, any primer pair derived from SEQ ID NO:3 or SEQ ID NO:4 that in a DNA amplification reaction produces an amplicon diagnostic for MON88017 or progeny thereof is an aspect of the present invention. Any single isolated DNA polynucleotide primer molecule comprising at least 11 contiguous nucleotides of SEQ ID NO:3, or its complement that is useful in a DNA amplification method to produce an amplicon diagnostic for MON88017 is an aspect of the invention. Any single isolated DNA polynucleotide primer molecule comprising at least 11 contiguous nucleotides of SEQ ID NO:4, or its complement that is useful in a DNA amplification method to produce an amplicon diagnostic for MON88017 is an aspect of the invention. An example of the amplification conditions for this analysis is illustrated in Table 2 and Table 3, however, any modification of these methods or the use DNA primers homologous or complementary to SEQ ID NO:3 or SEQ ID NO:4 or DNA sequences of the genetic elements contained in the transgene insert (SEQ ID NO:5) of MON88017 that produce an amplicon diagnostic for MON88017, is within the art. A diagnostic amplicon comprises a DNA molecule homologous or complementary to at least one transgene/genomic junction DNA (SEQ ID NO:1 or SEQ ID NO:2) or a substantial portion thereof.

An analysis for event MON88017 plant tissue sample should include a positive tissue control from event MON88017, a negative control from a corn plant that is not event MON88017, and a negative control that contains no corn genomic DNA. A primer pair that will amplify an endogenous corn DNA molecule will serve as an internal control for the DNA amplification conditions, an example of these are SEQ ID NO:28 and SEQ ID NO:29 that amplifies an approximately 239 bp DNA fragment. Additional primer sequences can be selected from SEQ ID NO:3, SEQ ID NO:4, or SEQ ID NO:5 by those skilled in the art of DNA amplification methods, and conditions selected for the production of an amplicon by the methods shown in Table 2 and Table 3 may differ, but result in an amplicon diagnostic for event MON88017 DNA. The use of these DNA primer sequences with modifications to the methods of Table 2 and 3 are within the scope of the invention. The amplicon produced by at least one DNA primer sequence derived from SEQ ID NO:3, SEQ ID NO:4, or SEQ ID NO:5 that is diagnostic for MON88017 is an aspect of the invention.

DNA detection kits that contain at least one DNA primer derived from SEQ ID NO:3 or SEQ ID NO:4, or SEQ ID NO:5 that when used in a DNA amplification method produces a diagnostic amplicon for MON88017 is an aspect of the invention. A corn plant or seed, wherein its genome will produce an amplicon diagnostic for MON88017 when tested in a DNA amplification method is an aspect of the invention. The assay for the MON88017 amplicon can be performed by using a Stratagene Robocycler, MJ Engine, Perkin-Elmer 9700, or Eppendorf Mastercycler Gradient thermocycler as shown in Table 3, or by methods and apparatus known to those skilled in the art.

TABLE 2

PCR procedure and reaction mixture conditions for the identification of MON88017 the 5' transgene insert/genomic junction region.

| Step | Reagent | Amount | Comments |
|---|---|---|---|
| 1 | Nuclease-free water | add to final volume of 20 µl | — |
| 2 | 10X reaction buffer (with MgCl$_2$) | 2.0 µl | 1X final concentration of buffer, 1.5 mM final concentration of MgCl$_2$ |
| 3 | 10 mM solution of dATP, dCTP, dGTP, and dTTP | 0.4 µl | 200 µM final concentration of each dNTP |
| 4 | event primer 1 (SEQ ID NO: 6) (resuspended in 1X TE buffer or nuclease-free water to a concentration of 10 µM) | 0.4 µl | 0.2 µM final concentration |
| 5 | event primer 2 (SEQ ID NO: 7) (resuspended in 1X TE buffer or nuclease-free water to a concentration of 10 µM) | 0.4 µl | 0.2 µM final concentration |
| 6 | RNase, DNase free (500 ng/µl) | 0.1 µl | 50 ng/reaction |
| 7 | REDTaq DNA polymerase (1 unit/µl) | 1.0 µl (recommended to switch pipets prior to next step) | 1 unit/reaction |
| 8 | Extracted DNA (template): Samples to be analyzed individual leaves pooled leaves (maximum of 20 leaves/pool) Negative control  Negative control Positive control | 10-200 ng of genomic DNA 200 ng of genomic DNA 50 ng of corn genomic DNA (not MON88017) no template DNA 50 ng of MON88017 genomic DNA | — |
| 9 | Gently mix and add 1-2 drops of mineral oil on top of each reaction. | | |

TABLE 3

Suggested PCR parameters for various commercially available thermocyclers.

| Cycle No. | |
|---|---|
| | Settings: Stratagene Robocycler |
| 1 | 94° C. 3 minutes |
| 38 | 94° C. 30 seconds |
| | 59° C. 1 minute |
| | 72° C. 1 minute |
| 1 | 72° C. 10 minutes |
| | Settings: MJ Engine, Perkin-Elmer 9700 or Eppendorf Mastercycler Gradient |
| 1 | 94° C. 3 minutes |
| 38 | 94° C. 15 seconds |
| | 59° C. 30 seconds |
| | 72° C. 1 minute |
| 1 | 72° C. 10 minutes |

Proceed with the DNA amplification in a Stratagene Robocycler, MJ Engine, Perkin-Elmer 9700, or Eppendorf Mastercycler Gradient thermocycler using the following cycling parameters. The MJ Engine or Eppendorf Mastercycler Gradient thermocycler should be run in the calculated mode. Run the Perkin-Elmer 9700 thermocycler with the ramp speed set at maximum.

Example 5

Southern blot analysis was performed on genomic DNA was isolated from the MON88017 and control corn tissue as described in Example 3. Quantitation of DNA samples was performed using a Hoefer DyNA Quant 200 Fluorometer (Pharmacia, Uppsala, Sweden) with Roche molecular size marker IX as a DNA calibration standard.

Approximately 20 µg of genomic DNA from the test substance and 10 µg of genomic DNA from the control substance were used for restriction enzyme digestions. For the insert stability analysis, approximately 10 µg of genomic DNA from the test substance were used. Overnight digests were performed at 37° C. in a total volume of ~500 µl using 1.00 units of the appropriate restriction enzyme. After digestion, the samples were precipitated by adding 1/10 volume (50 µl) of 3 M NaOAc (pH 5.2) and 2 volumes (1 ml relative to the original digest volume) of 100% ethanol, followed by incubation in a −20° C. freezer for at least 30 minutes. The digested DNA was pelleted at maximum speed in a microcentrifuge, washed with 70% ethanol, dried, and re-dissolved in TE buffer.

DNA probes were prepared by PCR amplification of plant expression cassette portion of pMON53616 template DNA. Approximately 25 ng of each probe (except the NOS 3' and TaHsp17 3' polyadenylation sequences) were labeled with $^{32}$P-dCTP (6000 Ci/mmol) by a random priming method (RadPrime DNA Labeling System, Life Technologies). The NOS 3' and tahsp17 3' polyadenylation sequences were labeled by PCR using 25 ng of DNA probe template in the following manner: sense and antisense primers specific to the template (0.25 mM each); 1.5 mM MgCl2; 3 mM each of dATP, dGTP and dTTP; ~100 mCi of 32P-dCTP (6000 Ci/mmol); and 2.5 Units of Taq DNA polymerase in a final volume of 20 ml. The cycling conditions were as follows: 1 cycle at 94° C. for 3 minutes; 2 cycles at 94° C. for 45 seconds, 52° C. for 30 seconds, 72° C. for 2 minutes; and 1 cycle at 72° C. for 10 minutes. All radiolabeled probes were purified using a Sephadex G-50 column (Roche, Indianapolis, Ind.).

Synthetic DNA molecules for use as probes for marker assisted breeding methods or for the detection of the MON88017 DNA in a sample can be made comprising the DNA sequence of the transgene/genome junction DNA molecule described in SEQ ID NO:1 and SEQ ID NO:2 or a substantial portion thereof.

Example 6

The methods used to identify heterozygous from homozygous progeny containing event MON88017 are described in a zygosity assay for which examples of conditions are described in Table 4 and Table 5. The DNA primers used in the zygosity assay are primers (SEQ ID NO:30), (SEQ ID NO:31), (SEQ ID NO:32), 6FAM™ labeled primer (SEQ ID NO:33) and VIC™ labeled primer (SEQ ID NO:34), 6FAM and VIC are florescent dye products of Applied Biosystems (Foster City, Calif.) attached to the DNA primer.

SEQ ID NO:30, SEQ ID NO:31 and SEQ ID NO:32 when used in these reaction methods produce a DNA amplicon for non-transgenic corn, two DNA amplicons for heterozygous corn containing event MON88017 DNA, and a DNA amplicon for homozygous MON88017 corn that is distinct from any other non-MON88017 corn plant. The controls for this analysis should include a positive control from homozygous and heterozygous corn containing event MON88017 DNA, a negative control from non-transgenic corn, and a negative control that contains no template DNA. This assay is optimized for use with a Stratagene Robocycler, MJ Engine, Perkin-Elmer 9700, or Eppendorf Mastercycler Gradient thermocycler. Other methods and apparatus known to those skilled in the art that produce amplicons that identify the zygosity of the progeny of crosses made with MON88017 plants is within the skill of the art.

TABLE 4

Zygosity assay reaction solutions

| Step | Reagent | Amount | Comments |
|---|---|---|---|
| 1 | Nuclease-free water | add to 10 µl final volume | — |
| 2 | 2X Universal Master Mix (Applied Biosystems cat. # 4304437) | 5 µl | 1 X final concentration |
| 3 | Primers SEQ ID NO: 30, 31, and 32 (resuspended in nuclease-free water to a concentration of 20 µM) | 0.5 µl | 0.25 µM final concentration |
| 4 | Primer 6FAM ™ (resuspended in nuclease-free water to a concentration of 10 µM) | 0.2 µl | 0.4 µM final concentration |
| 5 | Primer VIC ™ (resuspended in nuclease-free water to a concentration of 10 µM) | 0.2 µl | 0.15 µM final concentration |

TABLE 4-continued

Zygosity assay reaction solutions

| Step | Reagent | Amount | Comments |
|---|---|---|---|
| 6 | REDTaq DNA polymerase (1 unit/μl) | 1.0 μl (recommended to switch pipets prior to next step) | 1 unit/reaction |
| 7 | Extracted DNA (template): Samples to be analyzed (individual leaves) | 3.0 μl 4-80 ng of genomic DNA | Diluted in water |
|  | Negative control | 4 ng of non-transgenic corn genomic DNA |  |
|  | Negative control | no DNA template (solution in which DNA was resuspended) |  |
|  | Positive control | 4 ng of genomic DNA from known event MON88017 heterozygous corn |  |
|  | Positive control | 4 ng of genomic DNA from known event MON88017 homozygous corn |  |
| 8 | Gently mix, add 1-2 drops of mineral oil on top of each reaction. |  |  |

TABLE 5

Zygosity assay thermocycler conditions

| Cycle No. | |
|---|---|
| | Settings: Stratagene Robocycler |
| 1 | 94° C. 3 minutes |
| 38 | 94° C. 1 minute |
| | 60° C. 1 minute |
| | 72° C. 1 minute and 30 seconds |
| 1 | 72° C. 10 minutes |
| | Settings: MJ Engine or Perkin-Elmer 9700 |
| 1 | 94° C. 3 minutes |
| 38 | 94° C. 30 seconds |
| | 60° C. 30 seconds |
| | 72° C. 1 minute and 30 seconds |
| 1 | 72° C. 10 minutes |
| | Settings: Eppendorf Mastercycler Gradient |
| 1 | 94° C. 3 minutes |
| 38 | 94° C. 15 seconds |
| | 60° C. 15 seconds |
| | 72° C. 1 minute and 30 seconds |
| 1 | 72° C. 10 minutes |

Proceed with the DNA amplification in a Stratagene Robocycler, Mi Engine, Perkin-Elmer 9700, or Eppendorf Mastercycler Gradient thermocycler using the following cycling parameters. When running the PCR in the Eppendorf Mastercycler Gradient or MJ Engine, the thermocycler should be run in the calculated mode. When running the PCR in the Perkin-Elmer 9700, run the thermocycler with the ramp speed set at maximum.

A deposit of corn seed comprising event MON88017 disclosed above and recited in the claims, has been made under the Budapest Treaty with the American Type Culture Collection (ATCC), 10801 University Boulevard, Manassas, Va. 20110. The ATCC deposit was made on Oct. 10, 2003. The ATCC accession number is PTA-5582. The deposit will be maintained in the depository for a period of 30 years, or 5 years after the last request, or for the effective life of the patent, whichever is longer, and will be replaced as necessary during that period.

Example 7

Products such as foodstuffs and commodities can be produced from corn event MON88017, and such foodstuffs and commodities are expected to contain nucleotide sequences that, if detected in sufficient levels in such foodstuffs and commodities, can be diagnostic for the presence of corn event MON88017 materials within such commodities and foodstuffs. Examples of such foodstuffs and commodities include but are not limited to corn oil, corn meal, corn flour, corn gluten, corn cakes, corn starch, and any other foodstuff intended for consumption as a food source by an animal or otherwise, intended as a bulking agent, or intended as a component in a makeup composition for cosmetic use, etc. A nucleic acid detection method and/or kit based on a probe or a primer pair wherein the probe sequence or the sequence of the primers are selected from the group of sequences as set forth in SEQ ID NO:1, SEQ ID NO:2, SEQ ID NO:3, SEQ ID NO:4, and SEQ ID NO:5 may be developed that allows the detection of a MON88017 nucleotide sequence such as SEQ ID NO:1 or SEQ ID NO:2 in a biological sample, and such detection would be diagnostic for the corn event MON88017 in such sample.

Having illustrated and described the principles of the present invention, it should be apparent to persons skilled in the art that the invention can be modified in arrangement and detail without departing from such principles. We claim all modifications that are within the spirit and scope of the appended claims.

All publications and published patent documents cited in this specification are incorporated herein by reference to the same extent as if each individual publication or patent application was specifically and individually indicated to be incorporated by reference.

What is claimed is:

1. A recombinant DNA molecule comprising a nucleic acid sequence encoding a CRY3Bb1 protein and a CP4 EPSPS protein, said recombinant DNA molecule comprising a sequence selected from the group consisting of SEQ ID NO:1, SEQ ID NO:2, SEQ ID NO:3, SEQ ID NO:4 and SEQ ID NO:5, or a full complement thereof.

2. A composition comprising a pair of DNA primer molecules comprising a first DNA molecule and a second DNA molecule different from the first DNA molecule, wherein said first DNA molecule comprises a nucleotide sequence of sufficient length of contiguous nucleotides of a transgene insert DNA sequence of SEQ ID NO:5, or a full complement thereof and said second DNA molecule comprises a nucleotide sequence of sufficient length of contiguous nucleotides of the maize genomic DNA sequence of SEQ ID NO:3 or SEQ ID NO:4, to function as DNA primers when used together in a DNA amplification method to produce an amplicon diagnostic for corn event MON88017 DNA, wherein the amplicon comprises SEQ ID NO:1 or SEQ ID NO:2.

3. The recombinant DNA molecule of claim 1, comprising the nucleic acid sequence of SEQ ID NO:1.

4. The recombinant DNA molecule of claim 1, comprising the nucleic acid sequence of SEQ ID NO:2.

5. The recombinant DNA molecule of claim 1, comprising the nucleic acid sequence of SEQ ID NO:3.

6. The recombinant DNA molecule of claim 1, comprising the nucleic acid sequence of SEQ ID NO:4.

7. The recombinant DNA molecule of claim 1, comprising the nucleic acid sequence of SEQ ID NO:5.

8. A transgenic corn plant, seed, or part thereof comprising a DNA molecule comprising the nucleotide sequence of SEQ ID NO:5.

9. The transgenic corn plant, seed, or part thereof of claim 8, wherein the part comprises pollen, ovule, seed, roots, or leaves.

10. A commodity or foodstuff produced from the transgenic corn plant, seed, or part thereof of claim 8 and comprising a DNA molecule comprising a nucleic acid sequence selected from the group consisting of SEQ ID NO:1, SEQ ID NO:2, SEQ ID NO:3, SEQ ID NO:4 and SEQ ID NO:5, or a full complement thereof.

11. The commodity or foodstuff of claim 10, selected from the group consisting of corn oil, corn starch, corn meal, corn flour, a cosmetic, and a bulking agent.

* * * * *

SEQUENCE LISTING

<160> NUMBER OF SEQ ID NOS: 34

<210> SEQ ID NO 1
<211> LENGTH: 20
<212> TYPE: DNA
<213> ORGANISM: artificial sequence
<220> FEATURE:
<223> OTHER INFORMATION: Chimeric DNA of Zea mays genome and non Zea
      mays transgene insert

<400> SEQUENCE: 1
tgacggtgac gatatattca                                                     20

<210> SEQ ID NO 2
<211> LENGTH: 20
<212> TYPE: DNA
<213> ORGANISM: artificial sequence
<220> FEATURE:
<223> OTHER INFORMATION: chimeric DNA of Zea mays genome and non Zea
      mays transgene insert DNA

<400> SEQUENCE: 2
cagtttaaac agagtcgggt                                                     20

<210> SEQ ID NO 3
<211> LENGTH: 1461
<212> TYPE: DNA
<213> ORGANISM: artificial sequence
<220> FEATURE:
<223> OTHER INFORMATION: Chimeric DNA of Zea mays genome and non Zea
      mays transgene insert DNA

<400> SEQUENCE: 3
gaccagcgtc tcccgccgca cccgcagtct gcaccgtaga gatcggatgt acaggcatgt         60
agcattaggc tattcagcgg ctctcgtatc ttattcccta ccatctatttt tatctacact        120 gtataatact ccctccgttt attgtttatt tgtcgttgaa tagttcaata tttgcactgt        180
ccagcgacaa ctaaaatgaa acggagtgag gtagtgtttt gtacaaccat atatagaggt        240
gcccaaacgg gcggcccggc ccgggcccgt caggcccgac ggttaatcgg gccgtgcccg        300
gccggccccg tgccgtagcc gtggcccagg cacggcgtgc cgggccagcc gtttaactgg        360
tcacgttctc ccgcctaact gaaggacact aaccaatata actcgtgagc atttgttgta        420
aatagctaat ataaaatgta aatatatata ctatgtttta taaataaaa atatataat         480 cgtgccggcc aggccggcac tgcgggccaa gacagcggcc caagcacgtc acggttctcg        540
tgccgggccg gccccggcat cgtgtttcag gccggtccgt taggcacggc tcatttggcc        600
ctctataacc atatatcata ttcatcgacg accttgggct aaggcagacc gacggccgcc        660
ctaggcccca gatctataga ggcttaatgc taaatataaa ttcagtagtt agactatcaa        720
tgtatgatat aatagtttag caacaaaata ctaaagaatt tatggctacg atgttttcat        780
aatccgatct tatctaaaca tgttagaagg aaattttaaa gtaatattat aatatgtatc        840
tttttattta cttattgctt gatatagata ttttttgatct atcttaagtg ttttatattg       900
ataatattta tgtatataaa gaattagaat agtcctatt taaattttgt cctgaacccc        960
taaaatccca ggaccgccac ctatcatata catacatgat cttctaaata cccgatcaga       1020
gcgctaagca gcagaatcgt gtgacaacgc tagcagctct cctccaacac atcatcgaca       1080
agcacctttt ttgccggagt atgacggtga cgatatattc aattgtaaat ggcttcatgt       1140
ccgggaaatc tacatggatc agcaatgagt atgatggtca atatggagaa aaagaaagag       1200

```
taattaccaa ttttttttca attcaaaaat gtagatgtcc gcagcgttat tataaaatga    1260
aagtacattt tgataaaacg acaaattacg atccgtcgta tttataggcg aaagcaataa    1320
acaaattatt ctaattcgga aatctttatt tcgacgtgtc tacattcacg tccaaatggg    1380
ggcttagatg agaaacttca cgatttggcg cgccaaagct tactcgaggt cattcatatg    1440
cttgagaaga gagtcgggat a                                              1461
```

```
<210> SEQ ID NO 4
<211> LENGTH: 3525
<212> TYPE: DNA
<213> ORGANISM: artificial sequence
<220> FEATURE:
<223> OTHER INFORMATION: Chimeric DNA of Zea mays genome and non Zea
      mays transgene insert DNA

<400> SEQUENCE: 4
```

```
caaactccac atgggcttct cgggcgacaa gaatgaactg atcattggtg ctgagtcctt     60
cgtctccaac gagaagatct acatcgacaa gatcgagttc atcccgtcc agctgtgata    120 ggaactctga ttgaattctg catgcgtttg gacgtatgct cattcaggtt ggagccaatt    180
tggttgatgt gtgtgcgagt tcttgcgagt ctgatgagac atctctgtat tgtgtttctt    240
tccccagtgt tttctgtact tgtgtaatcg gctaatcgcc aacagattcg gcgatgaata    300
aatgagaaat aaattgttct gattttgagt gcaaaaaaaa aggaattaga tctgtgtgtg    360
ttttttggat ccccggggcg gccgctcgag caggacctgc agaagctagc ttgatgggga    420
tcagattgtc gtttcccgcc ttcagtttaa acagagtcgg gtttggatgg tcaactccgg    480
catactgccg aaaacaaacc aatccgtcac cgtcaaggcc ccgcaccgct ggccgcacgc    540
aggaaaaata agttgcgacc gcgagcgggc gaatcagaaa gggcgtccgg ccttggtcag    600 acacgcacagc gacgcggaaa ggctgcgccc gcggtgccat ctacaagggt ccacgtccat    660
ccaaaaagag cggtgccctg gacttctccc tcgtgttcct acttcctacg cgaaggaagc    720
caggcaggtg cgcagctttt ccaaccttcc acccccccg tgcggcgctc ccacgctgag    780
tcgctgaccg ctcgcgcctc tcttcgcctc tcctcactc gccgcgtcct ccgcagcaca    840
gcccactcgc atcggatcgc gcgcggggag cggcatggcc ggcgacgacg gcagcggcgg    900
gagcggaggc ggcaacaggg aggacgaggt ccacgtgcag atcgcaggtc agtgtcagtc    960
ctccgctcgt tctctctctc tccgacggac agtgtgaact atgtcgggtc gtcgttgagg   1020
atgcgatgag aggagcgcgg gaaggactgt cgtagattgg atttgctctg cagtgcgtgg   1080
gtagccccga gtccccgaca catgttcttt tttctcgggt tatgtcagcg gcggtacgtc   1140 gttgaacgc tcaagcgcga gaggtgttcg atgaattacc ttctggtgtg tggcgtaccg    1200
gtgggtcagt ggggttttttg gttcgtgtac gggatttggg gttggggggtc atctcccttc   1260 ttcagtgcgc gcgctcacga gtcacggctg tcttgtgatt gctgcatctg tgccatgtgc   1320
tcgtgcgtgc gttttcagtt actggccatt gacactgagt gaatgttcgg ttggtcgtcc   1380 gataggggttg gttcagctgt taattacgac tccaagtatc tgaaacattt catgaggatg   1440
tgtagggaac cttactttat gcacttcaat ggccaggcca ggcctgtatt atcttttttct   1500 tgtttgggaa taatgatgtg agctttaggg gagcagcgct gcttcttctt ttttttttct   1560
ccagaaaaag tcatagatat accgtggaca atttctttgt gtgcggtaat tttagagcac   1620
tgtgggtttg tgccctgttc gtcaggaaaa gtaccaagc tgggatttca cttgggtcta   1680
agaaaccagc gtttcagttt gggggggtctc ctggtaccct gaagtgctta ccatttatag   1740
```

```
ttcccggatg acctgttcat aatgccttct gtatgttgtt tgcaggatca tccaaacctg    1800
aaacctcatc taccaacgaa acagctcctc aaaactctca taccaagcat ggcattggt     1860 ggctgatggt aactctgaac attttcttcc tcgttgctgg tcagacagca tcgacactcc    1920
ttggcaggtt ctactacaac caaggtggaa atagcaagtg gatgtccaca tttgtccaaa    1980
ccgctggctt tccagtgctg ttcgtcgccc tatatctgtt ccgttcaaaa tcgccttcta    2040
cacaaacaac caccagtaac cctgagactt ctgtcaccaa aattactctt atatatgttg    2100
tcttgggcct catcattgct gccgatgact tgatgtattc ctatggcctg ttgtaccttc    2160
ctgtatcaac atattcgctc atttgcgcta gtcagctggc cttcaatgct gtcttctcat    2220
atgtcctaaa tgctcaaaag ttcaccccat tcattttcaa ctcagtaatt ctccttactt    2280
ttcccgctgc gcttcttgga gttgacgaag attctcaggg taccaatggt ttatcgcgtg    2340
ggaagtacat attgggtttc gcattgaccc taggagcctc ggccacatac tcactaattc    2400
tctctctaat gcaagtcgca ttcgagaagg ttattaagaa ggaaactttc tcagtcgtgt    2460
tgaatatgca gatatataca gcactagtgg caacagtagc ttctcttatc ggtttatttg    2520
caagcggcga gtggaagact ttagagggag agatgcatgc cttcagctca gggagggtgt    2580
cctatgtgat gacacttcta tggactgctg tatcttggca gatagcttcc gtaggagtgg    2640
tgggtttgat ctttgttgtg tcatcactct tttcaaatgt gataagcaca ctggctctac    2700
ccatcattcc gatttttgct gtgattttct tccacgacaa gatggatgga gtgaagatta    2760
ttgctatgtt gatggccatc tggggattcg tttcatatgg atatcaatta tatgtcagtg    2820
acaagaaggc taggaagact tcagtcagtg tggaggagaa ttcctaagcg cttgttggcc    2880
tgttacattg gtctttgtgg ctcctatacc actttaagtt gctggtattg aggaggtact    2940
agttattgac ttattgtatc caaaaggagc tcagttgaga atctcaggtt tacacaattc    3000
ataggtatat acttctgtta gtattgtcat atcatcatat gtaccgatgt acggttgtgt    3060
tgtcctttaa aataaaaaga ttagcatttc cagaggcatg ctctctagat ttctaattgc    3120
cttaaatatt ttcttgcctt tgttttgttt ttttttttt gctattaact gtgatttgtg     3180
attctatggt ttgacatata gtatttctag gtggtgtgca tgctgatcct gcttattcta    3240
ctatgaatta aatgcagtat aggtccatta acttttgcat gcgagcttct tggtgaaagc    3300
cctgcgtggt ttggttttga taactgagtg acagttagta aaggtttttt gtgtaccaca    3360
ttttcttagt gttcttcact ccaaatttga taggcgaggc tcgatcttat tcagttgctt    3420
ggctttcctt gttataacgc ctcagctaat ctggctttgt ttccttatgc ataccttctg    3480
taatctaaca ccaaaccaca gatgttgcat gtccattctc catgg                    3525
```

<210> SEQ ID NO 5
<211> LENGTH: 7450
<212> TYPE: DNA
<213> ORGANISM: artificial sequence
<220> FEATURE:
<223> OTHER INFORMATION: Chimeric DNA of Zea mays genome and non Zea
      mays transgene insert DNA

<400> SEQUENCE: 5

```
tacccgatca gagcgctaag cagcagaatc gtgtgacaac gctagcagct ctcctccaac      60
acatcatcga caagcacctt ttttgccgga gtatgacggg gacgatatat tcaattgtaa     120
atggcttcat gtccgggaaa tctacatgga tcagcaatga gtatgatggt caatatggag     180
aaaaagaaag agtaattacc aatttttttt caattcaaaa atgtagatgt ccgcagcgtt     240
attataaaat gaaagtacat tttgataaaa cgacaaatta cgatccgtcg tatttatagg     300
```

```
cgaaagcaat aaacaaatta ttctaattcg gaaatctttta tttcgacgtg tctacattca    360
cgtccaaatg ggggcttaga tgagaaactt cacgatttgg cgcgccaaag cttactcgag    420
gtcattcata tgcttgagaa gagagtcggg atagtccaaa ataaaacaaa ggtaagatta    480
cctggtcaaa agtgaaaaca tcagttaaaa ggtggtataa agtaaaatat cggtaataaa    540
aggtggccca aagtgaaatt tactcttttc tactattata aaaattgagg atgttttgt     600 cggtactttg atacgtcatt tttgtatgaa ttggtttta agtttattcg cttttggaaa     660
tgcatatctg tatttgagtc gggttttaag ttcgtttgct tttgtaaata cagagggatt    720
tgtataagaa atatctttag aaaaacccat atgctaattt gacataattt ttgagaaaaa    780
tatatattca ggcgaattct cacaatgaac aataataaga ttaaaatagc tttcccccgt    840
tgcagcgcat gggtattttt tctagtaaaa ataaaagata aacttagact caaaacattt    900
acaaaaacaa cccctaaagt tcctaaagcc caaagtgcta ccacgatccc atagcaagcc    960
cagcccaacc caacccaacc caacccaccc cagtccagcc aactggacaa tagtctccac   1020 accccccac tatcaccgtg agttgtccgc acgcaccgca cgtctcgcag ccaaaaaaaa    1080
aaagaaagaa aaaaaagaaa aagaaaaaac agcaggtggg tccgggtcgt gggggccgga   1140
aacgcgagga ggatcgcgag ccagcgacga ggccggccct ccctccgctt ccaaagaaac   1200
gccccccatc gccactatat acataccccc ccctctcctc ccatcccccc aaccctacca   1260
ccaccaccac caccacctcc acctcctccc ccctcgctgc cggacgacga gctcctcccc   1320 cctcccctc cgccgccgcc gcgccggtaa ccaccccgcc cctctcctct ttctttctcc    1380 gtttttttt ccgtctcggt ctcgatcttt ggccttggta gtttgggtgg gcgagaggcg    1440
gcttcgtgcg cgcccagatc ggtgcgcggg aggggcggga tctcgcggct ggggctctcg   1500
ccggcgtgga tccggcccgg atctcgcggg gaatggggct ctcggatgta gatctgcgat   1560
ccgccgttgt tgggggagat gatgggggt ttaaaatttc cgccgtgcta aacaagatca    1620
ggaagagggg aaaagggcac tatggtttat attttatat atttctgctg cttcgtcagg    1680
cttagatgtg ctagatcttt cttctcttctt tttgtgggta gaatttgaat ccctcagcat   1740
tgttcatcgg tagttttct tttcatgatt tgtgacaaat gcagcctcgt gcggagcttt    1800
tttgtaggta gaagtgatca accatggcgc aagttagcag aatctgcaat ggtgtgcaga   1860
acccatctct tatctccaat ctctcgaaat ccagtcaacg caaatctccc ttatcggttt    1920
ctctgaagac gcagcagcat ccacgagctt atccgatttc gtcgtcgtgg ggattgaaga   1980
agagtgggat gacgttaatt ggctctgagc ttcgtcctct taaggtcatg tcttctgttt   2040
ccacggcgtg catgcttcac ggtgcaagca gccggcccgc aaccgcccgc aaatcctctg   2100 gccttccgg aaccgtccgc attcccggcg acaagtcgat ctcccaccgg tccttcatgt    2160
tcggcggtct cgccgagcggt gaaacgcgca tcaccggcct tctggaaggc gaggacgtca   2220
tcaatacggg caaggccatg caggcgatgg gcgcccgcat ccgtaaggaa ggcgacacct   2280
ggatcatcga tggcgtcggc aatgcggcc tcctggcgcc tgaggcgccg ctcgatttcg    2340
gcaatgccgc cacgggctgc cgcctgacga tgggcctcgt cggggtctac gatttcgaca   2400
gcaccttcat cggcgacgcc tcgctcacaa agcgcccgat gggccgcgtg ttgaacccgc   2460
tgcgcgaaat gggcgtgcag gtgaaatcgg aagacgtga ccgtcttccc gttaccttgc    2520
gcgggccgaa gacgccgacg ccgatcacct accgcgtgcc gatggcctcc gcacaggtga   2580
agtccgccgt gctgctcgcc ggcctcaaca cgcccggcat cacgacgtc atcgagccga    2640 tcatgacgcg cgatcatacg gaaaagatgc tgcagggctt tggcgccaac cttaccgtcg   2700
```

```
agacggatgc ggacggcgtg cgcaccatcc gcctggaagg ccgcggcaag ctcaccggcc    2760
aagtcatcga cgtgccgggc gacccgtcct cgacggcctt cccgctggtt gcggccctgc    2820
ttgttccggg ctccgacgtc accatcctca acgtgctgat gaaccccacc cgcaccggcc    2880
tcatcctgac gctgcaggaa atgggcgccg acatcgaagt catcaacccg cgccttgccg    2940
gcggcgaaga cgtggcggac ctgcgcgttc gctcctccac gctgaagggc gtcacggtgc    3000
cggaagaccg cgcgccttcg atgatcgacg aatatccgat tctcgctgtc gccgccgcct    3060
tcgcggaagg ggcgaccgtg atgaacggtc tggaagaact ccgcgtcaag gaaagcgacc    3120
gcctctcggc cgtcgccaat ggcctcaagc tcaatggcgt ggattgcgat gagggcgaga    3180
cgtcgctcgt cgtgcgtggc cgccctgacg gcaaggggct cggcaacgcc tcgggcgccg    3240
ccgtcgccac ccatctcgat caccgcatcg ccatgagctt cctcgtcatg ggcctcgtgt    3300
cggaaaaccc tgtcacggtg gacgatgcca cgatgatcgc cacgagcttc ccggagttca    3360
tggacctgat ggccgggctg ggcgcgaaga tcgaactctc cgatacgaag gctgcctgat    3420
gagctcgaat tcccgatcgt tcaaacattt ggcaataaag tttcttaaga ttgaatcctg    3480
ttgccggtct tgcgatgatt atcatataat ttctgttgaa ttacgttaag catgtaataa    3540
ttaacatgta atgcatgacg ttatttatga gatgggtttt tatgattaga gtcccgcaat    3600
tatacattta atacgcgata gaaaacaaaa tatagcgcgc aaactaggat aaattatcgc    3660
gcgcggtgtc atctatgtta ctagatcggg gatttgcggc cgcgttaaca agcttctgca    3720
ggtccgattg agacttttca acaaagggta atatccggaa acctcctcgg attccattgc    3780
ccagctatct gtcactttat tgtgaagata gtggaaaagg aaggtggctc ctacaaatgc    3840
catcattgcg ataaaggaaa ggccatcgtt gaagatgcct ctgccgacag tggtcccaaa    3900
gatggacccc cacccacgag gagcatcgtg aaaaagaag acgttccaac cacgtcttca    3960
aagcaagtgg attgatgtga tggtccgatt gagacttttc aacaaagggt aatatccgga    4020
aacctcctcg gattccattg cccagctatc tgtcacttta ttgtgaagat agtggaaaag    4080
gaaggtggct cctacaaatg ccatcattgc gataaaggaa aggccatcgt tgaagatgcc    4140
tctgccgaca gtggtcccaa agatggaccc ccacccacga ggagcatcgt ggaaaaagaa    4200
gacgttccaa ccacgtcttc aaagcaagtg gattgatgtg atatctccac tgacgtaagg    4260
gatgacgcac aatcccacta ccttcgcaa gacccttcct ctatataagg aagttcattt    4320
catttggaga ggacacgctg acaagctgac tctagcagat cctctagaac catcttccac    4380
acactcaagc cacactattg gagaacacac agggacaaca caccataaga tccaagggag    4440
gcctccgccg ccgccggtaa ccaccccgcc cctctcctct ttctttctcc gttttttttt    4500
ccgtctcggt ctcgatcttt ggccttggta gtttgggtgg gcgagaggcg gcttcgtgcg    4560
cgcccagatc ggtgcgcggg aggggcggga tctcgcggct ggggctctcg ccggcgtgga    4620
tccggcccgg atctcgcggg gaatgggggt ctcggatgta gatctgcgat ccgccgttgt    4680
tgggggagat gatgggggt ttaaaatttc cgccgtgcta aacaagatca ggaagagggg    4740
aaaagggcac tatggtttat atttttatat atttctgctg cttcgtcagg cttagatgtg    4800
ctagatcttt ctttcttctt tttgtgggta gaatttgaat ccctcagcat tgttcatcgg    4860
tagtttttct tttcatgatt tgtgacaaat gcagcctcgt gcggagcttt tttgtaggta    4920
gaagtgatca accatggcca accccaacaa tcgctccgag cacgacacga tcaaggtcac    4980
ccccaactcc gagctccaga ccaaccacaa ccagtacccg ctggccgaca accccaactc    5040
caccctggaa gagctgaact acaaggagtt cctgcgcatg accgaggact cctccacgga    5100
```

```
ggtcctggac aactccaccg tcaaggacgc cgtcgggacc ggcatctccg tcgtttgggca   5160
gatcctgggc gtcgttggcg tcccccttcgc aggtgctctc acctccttct accagtcctt   5220
cctgaacacc atctggccct ccgacgccga cccctggaag gccttcatgg cccaagtcga   5280
agtcctgatc gacaagaaga tcgaggagta cgccaagtcc aaggccctgg ccgagctgca   5340
aggcctgcaa aacaacttcg aggactacgt caacgcgctg aactcctgga agaagacgcc   5400
tctgtccctg cgctccaagc gctcccagga ccgcatccgc gagctgttct cccaggccga   5460
gtcccacttc cgcaactcca tgccgtcctt cgccgtctcc aagttcgagg tcctgttcct   5520
gcccacctac gcccaggctg ccaacaccca cctcctgttg ctgaaggacg cccaggtctt   5580
cggcgaggaa tggggctact cctcggagga cgtcgccgag ttctaccgtc gccagctgaa   5640
gctgacccaa cagtacaccg accactgcgt caactggtac aacgtcggcc tgaacggcct   5700
gaggggctcc acctacgacg catgggtcaa gttcaaccgc ttccgcaggg agatgaccct   5760
gaccgtcctg gacctgatcg tcctgttccc cttctacgac atccgcctgt actccaaggg   5820
cgtcaagacc gagctgaccc gcgacatctt cacggacccc atcttcctgc tcacgaccct   5880
ccagaagtac ggtcccacct tcctgtccat cgagaactcc atccgcaagc cccacctgtt   5940
cgactacctc cagggcatcg agttccacac gcgcctgagg ccaggctact cggcaagga    6000
ctccttcaac tactggtccg gcaactacg cgagaccagg ccctccatcg gctcctcgaa    6060
gacgatcacc tcccctttct acggcgacaa gtccaccgag cccgtccaga gctgtccctt    6120
cgacggccaa aaggtctacc gcaccatcgc caacaccgac gtcgcggctt ggccgaacgg    6180
caaggtctac ctgggcgtca cgaaggtcga cttctcccag tacgatgacc agaagaacga    6240
gacctccacc cagacctacg actccaagcg caacaatggc cacgtctccg cccaggactc    6300
catcgaccag ctgccgcctg agaccactga cgagcccctg gagaaggcct actcccacca    6360
gctgaactac gcggagtgct tcctgatgca agaccgcagg ggcaccatcc ccttcttcac    6420
ctggacccac cgctccgtcg acttcttcaa caccatcgac gccgagaaga tcacccagct    6480
gcccgtggtc aaggcctacg ccctgtcctc gggtgcctcc atcattgagg tccaggcttt    6540
caccggtggc aacctgctgt tcctgaagga gtcctcgaac tccatcgcca agttcaaggt    6600
caccctgaac tccgctgcct tgctgcaacg ctaccgcgtc cgcatccgct acgcctccac    6660
cacgaacctg cgcctgttcg tccagaactc caacaatgac ttcctggtca tctacatcaa    6720
caagaccatg aacaaggacg atgacctgac ctaccagacc ttcgacctcg ccaccacgaa    6780
ctccaacatg ggcttctcgg gcgacaagaa tgaactgatc attggtgctg agtccttcgt    6840
ctccaacgag aagatctaca tcgacaagat cgagttcatc cccgtccagc tgtgatagga    6900
actctgattg aattctgcat gcgtttggac gtatgctcat tcaggttgga gccaatttgg    6960
ttgatgtgtg tgcgagttct tgcgagtctg atgagacatc tctgtattgt gtttctttcc    7020
ccagtgtttt ctgtacttgt gtaatcggct aatcgccaac agattcggcg atgaataaat    7080
gagaaataaa ttgttctgat tttgagtgca aaaaaaagg aattagatct gtgtgtgttt     7140
tttggatccc cggggcggcc gctcgagcag gacctgcaga agctagcttg atggggatca    7200
gattgtcgtt tcccgccttc agtttaaaca gagtcgggtt tggatggtca actccggcat    7260
actgccgaaa acaaaccaat ccgtcaccgt caaggccccg caccgctggc cgcacgcagg    7320
aaaaataagt tgcgaccgcg agcgggcgaa tcagaaaggg cgtccggcct tggtcagaca    7380
cgacagcgac gcggaaaggc tgcgcccgcg gtgccatcta caagggtcca cgtccatcca    7440
aaaagagcgg                                                          7450
```

```
<210> SEQ ID NO 6
<211> LENGTH: 21
<212> TYPE: DNA
<213> ORGANISM: Zea mays

<400> SEQUENCE: 6
ctgaacccct aaaatcccag g                                        21

<210> SEQ ID NO 7
<211> LENGTH: 30
<212> TYPE: DNA
<213> ORGANISM: Oryza sativa

<400> SEQUENCE: 7
cctttgtttt attttggact atcccgactc                               30

<210> SEQ ID NO 8
<211> LENGTH: 40
<212> TYPE: DNA
<213> ORGANISM: Triticum aestivum

<400> SEQUENCE: 8
ctgatgagac atctctgtta ttgtgtttct ttccccagtg                    40

<210> SEQ ID NO 9
<211> LENGTH: 30
<212> TYPE: DNA
<213> ORGANISM: Triticum aestivum

<400> SEQUENCE: 9
tgtaatcggc taatcgccaa cagattcggc                               30

<210> SEQ ID NO 10
<211> LENGTH: 32
<212> TYPE: DNA
<213> ORGANISM: Triticum aestivum

<400> SEQUENCE: 10
cggccgctcg agcaggacct gcagaagcta gc                            32

<210> SEQ ID NO 11
<211> LENGTH: 33
<212> TYPE: DNA
<213> ORGANISM: Triticum aestivum

<400> SEQUENCE: 11
gatggggatc agattgtcgt ttcccgcctt cag                           33

<210> SEQ ID NO 12
<211> LENGTH: 27
<212> TYPE: DNA
<213> ORGANISM: Oryza sativa

<400> SEQUENCE: 12
cactttgggc cacctttat taccgat                                   27

<210> SEQ ID NO 13
<211> LENGTH: 29
<212> TYPE: DNA
<213> ORGANISM: Oryza sativa

<400> SEQUENCE: 13
ctgatgtttt cacttttgac caggtaatc                                29
```

```
<210> SEQ ID NO 14
<211> LENGTH: 28
<212> TYPE: DNA
<213> ORGANISM: Oryza sativa

<400> SEQUENCE: 14
taattactct ttcttttct ccatattg                                         28

<210> SEQ ID NO 15
<211> LENGTH: 26
<212> TYPE: DNA
<213> ORGANISM: Oryza sativa

<400> SEQUENCE: 15
catactcatt gctgatccat gtagat                                          26

<210> SEQ ID NO 16
<211> LENGTH: 24
<212> TYPE: DNA
<213> ORGANISM: Zea mays

<400> SEQUENCE: 16
cctattttaa attttgtcct gaac                                            24

<210> SEQ ID NO 17
<211> LENGTH: 27
<212> TYPE: DNA
<213> ORGANISM: Oryza sativa

<400> SEQUENCE: 17
gatcgtggat agcactttgg gctttag                                         27

<210> SEQ ID NO 18
<211> LENGTH: 29
<212> TYPE: DNA
<213> ORGANISM: Zea mays

<400> SEQUENCE: 18
accgccacct atcatataca tacatgatc                                       29

<210> SEQ ID NO 19
<211> LENGTH: 27
<212> TYPE: DNA
<213> ORGANISM: Oryza sativa

<400> SEQUENCE: 19
aggtggccca aagtgaaatt tactctt                                         27

<210> SEQ ID NO 20
<211> LENGTH: 28
<212> TYPE: DNA
<213> ORGANISM: Arabidopsis thaliana

<400> SEQUENCE: 20
gcagatctac atccgagagc cccattcc                                        28

<210> SEQ ID NO 21
<211> LENGTH: 28
<212> TYPE: DNA
<213> ORGANISM: Oryza sativa

<400> SEQUENCE: 21
tcgatctttg gccttggtag tttgggtg                                        28
```

```
<210> SEQ ID NO 22
<211> LENGTH: 28
<212> TYPE: DNA
<213> ORGANISM: Agrobacterium tumefaciens

<400> SEQUENCE: 22
gctcatcagg cagccttcgt atcgggag                                      28

<210> SEQ ID NO 23
<211> LENGTH: 27
<212> TYPE: DNA
<213> ORGANISM: Agrobacterium tumefaciens

<400> SEQUENCE: 23
ctcgatcacc gcatcgccat gagcttc                                       27

<210> SEQ ID NO 24
<211> LENGTH: 28
<212> TYPE: DNA
<213> ORGANISM: Bacillus thuringiensis

<400> SEQUENCE: 24
aagacctggg cgtccttcag caacagga                                      28

<210> SEQ ID NO 25
<211> LENGTH: 28
<212> TYPE: DNA
<213> ORGANISM: Bacillus thuringiensis

<400> SEQUENCE: 25
cctggaaggc cttcatggcc caagtcga                                      28

<210> SEQ ID NO 26
<211> LENGTH: 27
<212> TYPE: DNA
<213> ORGANISM: Zea mays

<400> SEQUENCE: 26
aacagaggcg tgaccggtca gcgactc                                       27

<210> SEQ ID NO 27
<211> LENGTH: 28
<212> TYPE: DNA
<213> ORGANISM: Zea mays

<400> SEQUENCE: 27
tccttcgcgt aggaagtagg cacacgag                                      28

<210> SEQ ID NO 28
<211> LENGTH: 20
<212> TYPE: DNA
<213> ORGANISM: Zea mays

<400> SEQUENCE: 28
cgtggtgatc acaaacagta                                               20

<210> SEQ ID NO 29
<211> LENGTH: 21
<212> TYPE: DNA
<213> ORGANISM: Zea mays

<400> SEQUENCE: 29
ctatatgaca gacccatcgt t                                             21
```

-continued

```
<210> SEQ ID NO 30
<211> LENGTH: 20
<212> TYPE: DNA
<213> ORGANISM: Zea mays

<400> SEQUENCE: 30
cacatcatcg acaagcacct                                                   20

<210> SEQ ID NO 31
<211> LENGTH: 22
<212> TYPE: DNA
<213> ORGANISM: Zea mays

<400> SEQUENCE: 31
gtatgccgga gttgaccatc ca                                                22

<210> SEQ ID NO 32
<211> LENGTH: 24
<212> TYPE: DNA
<213> ORGANISM: Oryza sativa

<400> SEQUENCE: 32
ggacatgaag ccatttacaa ttga                                              24

<210> SEQ ID NO 33
<211> LENGTH: 15
<212> TYPE: DNA
<213> ORGANISM: artificial sequence
<220> FEATURE:
<223> OTHER INFORMATION: labeled primer for use in zygosity assay

<400> SEQUENCE: 33
tgacggtgac gatat                                                        15

<210> SEQ ID NO 34
<211> LENGTH: 15
<212> TYPE: DNA
<213> ORGANISM: artificial sequence
<220> FEATURE:
<223> OTHER INFORMATION: labeled primer for use in zygosity assay

<400> SEQUENCE: 34
agaaggccgg agtcg                                                        15
```